(12) United States Patent
Ridder et al.

(10) Patent No.: US 7,756,558 B2
(45) Date of Patent: Jul. 13, 2010

(54) APPARATUS AND METHODS FOR MITIGATING THE EFFECTS OF FOREIGN INTERFERENTS ON ANALYTE MEASUREMENTS IN SPECTROSCOPY

(75) Inventors: Trent Ridder, Woddbridge, VA (US); Shonn Hendee, Albuquerque, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 1237 days.

(21) Appl. No.: 11/305,964

(22) Filed: Dec. 19, 2005

(65) Prior Publication Data

US 2007/0142720 A1      Jun. 21, 2007

Related U.S. Application Data

(63) Continuation-in-part of application No. 10/852,415, filed on May 24, 2004, now Pat. No. 7,403,804.

(51) Int. Cl.
*A61B 5/1455*      (2006.01)
(52) U.S. Cl. ........................ 600/310; 600/316
(58) Field of Classification Search .......... 600/309–344
See application file for complete search history.

(56) References Cited

U.S. PATENT DOCUMENTS

| | | | |
|---|---|---|---|
| 5,830,132 A * | 11/1998 | Robinson | 600/310 |
| 6,424,848 B1 * | 7/2002 | Berman et al. | 600/316 |
| 6,493,566 B1 * | 12/2002 | Ruchti et al. | 600/310 |
| 6,788,965 B2 * | 9/2004 | Ruchti et al. | 600/310 |
| 7,167,735 B2 * | 1/2007 | Uchida et al. | 600/310 |
| 7,194,369 B2 * | 3/2007 | Lundstedt et al. | 702/104 |
| 7,403,804 B2 * | 7/2008 | Ridder et al. | 600/310 |
| 2005/0130321 A1 * | 6/2005 | Nicholson et al. | 436/518 |

* cited by examiner

*Primary Examiner*—Eric F Winakur
(74) *Attorney, Agent, or Firm*—V. Gerald Grafe

(57) ABSTRACT

The present invention includes apparatuses and methods for mitigating the effects of foreign interferents on analyte measurements. The present invention comprises several interferent mitigation steps. Examples include sample cleaning procedures, detection of the presence of interferents, determination of the identity of interferents, and modification or selection of a multivariate calibration model to mitigate the effects of one or more interferents on analyte measurements. The interferent mitigation steps of the present invention can be applied individually, and in some embodiments can be applied in combination. Some examples of relevant analyte measurements include the noninvasive determination of the presence or concentration of alcohol, glucose, urea, byproducts of alcohol metabolism, and substances of abuse.

24 Claims, 20 Drawing Sheets

APPARATUS AND METHODS FOR MITIGATING THE EFFECTS OF FOREIGN INTERFERENTS ON ANALYTE MEASUREMENTS IN SPECTROSCOPY

CROSS REFERENCES TO RELATED APPLICATIONS

This application claims priority under 35 U.S.C §120 as a continuation-in-part of U.S. patent application Ser. No. 10/852,415, now U.S. Pat. No. 7,403,804, entitled "Noninvasive determination of alcohol in tissue," filed May 24, 2004, incorporated herein by reference. This application is related to U.S. patent application Ser. No. 09/832,585, entitled "System For Non-Invasive Measurement Of Glucose In Humans," filed Apr. 11, 2001, and to U.S. patent application Ser. No. 10/281,576, entitled "Optically Similar Reference Samples", filed Dec. 28, 2002, and to U.S. patent application Ser. No. 10/378,237, entitled "System For Non-Invasive Measurement Of Glucose In Humans," filed Mar. 3, 2003, and to U.S. patent application Ser. No. 10/753,506, "Noninvasive Determination of Direction and Rate of Change of an Analyte," filed Jan. 8, 2004, each of which is incorporated herein by reference.

TECHNICAL FIELD

The present invention relates generally to measurement of one or more analytes, particularly relating to alcohol as an analyte contained in blood, tissue, or a bodily fluid, utilizing spectroscopic methods. More particularly, the invention discloses methods for mitigating the effects of foreign interferents on analyte measurements.

BACKGROUND OF THE INVENTION

Infrared spectroscopy is a generally known basis for analysis. In some forms, infrared spectroscopy measures the electromagnetic radiation (typical wavelength range of 0.7-25 µm) that a substance absorbs at various wavelengths, though other methods measure other effects a substance has on incident light. Absorption phenomena can be related to molecular vibrations and shifts in energy levels of individual atoms or electrons within a molecule. These phenomena cause the absorbing molecule or atom to switch to a higher energy state. Absorption occurs most frequently in limited ranges of wavelengths that are based upon the molecular structure of the species present in the measured sample. Thus, for light passing through a substance at several wavelengths, the substance will absorb a greater percentage of photons at certain wavelengths than it will at others. The characterization of substances by their spectral absorption characteristics is well known.

At the molecular level, many primary vibrational transitions occur in the mid-infrared wavelength region (i.e., wavelengths between 2.5-6 µm). However, for some measurements, such as the non-invasive measurement of analytes in tissue, use of the mid-infrared region can be problematic because molecules with strong absorbance properties (e.g. water) can result in the total absorption of virtually all light introduced to the sample being measured. The problem can be overcome through the use of shorter wavelengths (typically in the near infrared region of 0.7-2.5 µm) where weaker overtones and combinations of the mid-infrared vibrations exist. Thus, the near-infrared region is often employed in such situations as it preserves the qualitative and quantitative properties of mid-infrared measurements while helping to alleviate the problem of total light absorption.

As mentioned above, alcohol and other analytes absorb light at multiple frequencies in both the mid- and near-infrared range. Due to the overlapping nature of these absorption bands, reliable analyte measurements can be very difficult if only a single frequency or wavelength is used for analysis. Thus, analysis of spectral data often incorporates absorption characteristics at several wavelengths, which enables sensitive and selective analyte measurements. In multi-wavelength spectroscopy, multivariate analysis techniques are often used to empirically determine the relationship between measured spectra and a property of interest (e.g. analyte concentration).

Advances in optical materials and multivariate algorithms over the last several decades have created the potential for expanding spectroscopic measurements into new areas of interest. One such area is the noninvasive measurement of analytes such as alcohol in humans. The application of spectroscopic techniques to measurement of analyte properties such as alcohol concentration can be complicated by the presence of interferents. Interferents can mask or obscure the response due to alcohol, leading to false or misleading results. This problem is made more significant by the motivation of individuals to confound alcohol measurements in punitive settings such as traffic stops. A similar problem exists in spectroscopic measurement of other analytes, where, for example, interferents such as lotion or insect repellant can contribute to inaccurate results such as glucose concentration measurements. There is a need for apparatuses and methods to mitigate the effects of foreign interferents on spectroscopic measurements.

SUMMARY OF THE INVENTION

The present invention includes apparatuses and methods for mitigating the effects of foreign interferents on analyte measurements. The present invention comprises several interferent mitigation steps. Examples include sample cleaning procedures, detection of the presence of interferents, determination of the identity of interferents, and modification or selection of a multivariate calibration model to mitigate the effects of one or more interferents on analyte measurements. The interferent mitigation steps of the present invention can be applied individually, and in some embodiments can be applied in combination. For the purposes of this invention, the term "analyte measurement" generally refers to the concentration of said analyte in a sample, however, it is recognized that other properties, such as the rate of change of the analyte concentration or the detection of the presence of the analyte, can be measured in conjunction with or instead of the analyte concentration. Some examples of relevant analyte measurements include the noninvasive determination of the presence or concentration of alcohol, glucose, urea, byproducts of alcohol metabolism, and substances of abuse. The present invention addresses this need for analyte measurements of samples utilizing spectroscopy where the term "sample" generally refers to biological tissue, blood, or other bodily fluid that is to be measured in vivo, in vitro, or ex vivo. However, it is recognized that other types of samples can benefit from the present invention.

In some embodiments, a spectrum can be analyzed for abnormal spectral signature arising from one or more interferents prior to application of a multivariate calibration model to determine the desired analyte property. The interferent detection analysis can be performed using a variety of means such as comparison of the spectrum to a reference library of spectra that contain various interferents, examination of the residuals of a principal components analysis (PCA), or metrics such as the Mahalanobis Distance and spectral F-ratio (Q-Statistic). In some embodiments, the identity of the interferent or interferents does not need to be determined as knowledge of the presence of an interferent (and not the identity) can be sufficient information. For example, a measurement administrator can disqualify the affected sample and/or initiate a procedure to remove or clean the unknown interferent from the sample, at which point the sample can be re-measured.

In some embodiments, the identity of the interferent can be determined such that more specific instructions can be conveyed to the user or an automated mitigation step can be initiated. For example, if motor oil is determined to be on the surface of the sample, the present invention allows the user to be directed to use a motor oil-specific cleaning agent to remove the interferent from the sample. Furthermore, knowledge of the identity of one or more interferents allows the automatic or user initiated modification of, creation of a new, or selection of a different multivariate calibration model.

The step of detecting interferents can be omitted if it is determined that the mitigation methodologies are to be universally applied regardless of the presence of interferents or if the presence/effects of interferents are not relevant to the measurement. For example, a sample cleaning procedure can be established as part of the analyte measurement process in order to mitigate the effects of topical interferents. In this example, the sample cleaning procedure would be performed on all samples regardless of whether an interferent has been detected. This can be advantageous in situations where a consistent measurement protocol is necessary or more advanced mitigation methods are not warranted.

In some embodiments, cleaning the sample can be a step of the interferent mitigation method. It is recognized that the cleaning process can introduce an interferent to the sample. In some embodiments, this is an acceptable consequence of cleaning as it can effectively condenses an infinite number of potential interferents to those present in the cleaning agents. For example, the use of an isopropyl alcohol wipe will introduce isopropyl alcohol to the sample surface. In some embodiments, the effects of the introduced interferent on the measurement are negligible and can be ignored. In other embodiments, the interferent can be accounted for in the multivariate calibration model such that its spectral effects can be implicitly accommodated and the effects on the analyte measurement minimized.

In some embodiments, the sample cleaning procedure or identification of an interferent can dictate the selection of a specific multivariate calibration from a library of multivariate calibration models. For example, in noninvasive measurement of ethyl alcohol in tissue, an ethyl alcohol multivariate calibration that incorporated the interfering effects of isopropyl alcohol can be used in connection with the application of an isopropyl alcohol cleaning procedure to the tissue surface. Furthermore, the sample cleaning procedure can involve the use of more than one cleaning agent either in the same solution or applied sequentially. For example, cologne or perfume can be cleaned with one cleaning agent and grease might need a different cleaning agent. If both cologne and grease are present, both cleaning agents can be necessary. In addition, a single cleaning agent might be insufficient for a given interferent and therefore require repeating the cleaning procedure with either the same or a second cleaning agent. Alternatively, a "complete" cleaning agent can include all individual cleaning agents necessary to clean the majority of potential interferents.

The number of potential interferents can be large. As such it can be advantageous to categorize interferents in order to simplify the interferent mitigation method. The categories could be based on similarities in spectroscopic signal or in chemical structure or class. For example, motor oil and grease are chemically and spectrally similar and can be placed in the same category. Other example categories include alcohols, medications, and skin lotions. Suitable methods for assessing spectral similarity include, but are not limited to, classification methods such as K nearest neighbors, PCA, discriminant analysis, and neural networks. In some embodiments, interferents in the same category can be mitigated via the same method while other categories may receive alternative mitigation methods. These treatments can include multivariate calibration models designed to mitigate one or more interferent categories, sample cleaning steps, or a combination thereof.

If the identity or category of an interferent is determined and a suitable signal of the interferent or its effects is available, the multivariate calibration model can be modified or regenerated such that the effects of the interferent are incorporated. The signal can be derived from the measurement that the interferent is corrupting, or from a reference library of interferent signals or signals representing interferent classes. New calibration measurements that physically include the detected interferent can also be acquired such that a new multivariate calibration model can be generated, or an existing model can be updated.

Another aspect of modifying the calibration is to include or exclude wavelengths of light from the calibration data based upon knowledge of the interferent. The multivariate calibration model can then be regenerated and applied to the measured spectrum or subsequently measured spectra. In this manner, spectral regions dominated by the interferent can be excluded or additional wavelengths can be added to increase the amount of information available to resolve the interferent from the analyte.

As multiple interferents can be present in a measurement, any of the above methods or combinations of methods can be used sequentially or simultaneously to mitigate multiple interferents. It can be logistically difficult to acquire calibration data that incorporate all potential interferents and that mathematically including the pure component signals of a large number of interferents can be unnecessarily detrimental to the analyte measurement. However, such strategies are plausible if the resulting analyte measurement meets the needs of the user. An alternative approach to treating for all possible interferents is to determine a subset of interferents that represents the most significant threat to the analyte measurement and develop a suitable mitigation method. The magnitude of a threat can be assessed either through an interferent's effect on the analyte measurement, the likelihood of its presence in future samples, or a combination.

Another potential interferent mitigation method is to use a library of multivariate calibration models that are specifically designed to mitigate specific interferents, interferent categories, or common combinations of interferents or interferent categories. These multivariate calibration models can be pre-determined such that detection and identification of an interferent or combination of interferents allows selection of the appropriate pre-determined multivariate calibration model. This method allows a priori calibration data to be acquired with the desired interferent(s) included in the measured calibration samples thereby explicitly including the effects of the interferent(s) in the calibration.

In other embodiments, a library of pre-determined multivariate calibrations can be generated by combining interferent-free calibration data with various interferent signals in a manner similar to the mathematical combination approach discussed above. Similar to the mathematical combination approach, the calibrations within the library can also include or exclude different wavelength regions in order to mitigate interferents. A "library" multivariate calibration model can be designed to mitigate more than 1 interferent and this approach can be combined with one or more of the other mitigation methods described herein.

The above described interferent mitigation steps can involve cleaning interferents from the sample, various approaches for obtaining a multivariate calibration model that incorporates the effects of the interferent, or a combination thereof. Interferents can also be mitigated by optimizing the optical and mechanical design of the measurement device such that it has reduced susceptibility to interferents. For example, the materials used to fabricate the portion of the measurement device that interfaces with the sample can be chosen such that they are immune to contamination by certain classes of interferents. For example, as Teflon is known to absorb and hold water, it can be avoided in measurement devices where water contamination is a concern. Further, the optical design can be such that contact between the sensor element and sample is not necessary, thereby reducing the possibility of contamination of the sensor.

In other embodiments, the sensor can be designed such that the light is introduced and collected from the sample in a manner that minimizes travel through the interferent. For example, in noninvasive measurements of tissue, the measurement device can target the depth of the dermal layer of tissue in order to minimize the spectral contribution of topical interferents residing in the epidermis. Combinations of the above interferent mitigation methods can yield embodiments that result in better performance than any individual approach. For example, a measurement device incorporating materials and designs robust to interferent contamination is combined with a cleaning step and a multivariate calibration model that incorporating the spectral signature of the cleaning agents.

The advantages and features of novelty that characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

DETAILED DESCRIPTION OF THE INVENTION

Figure 1:
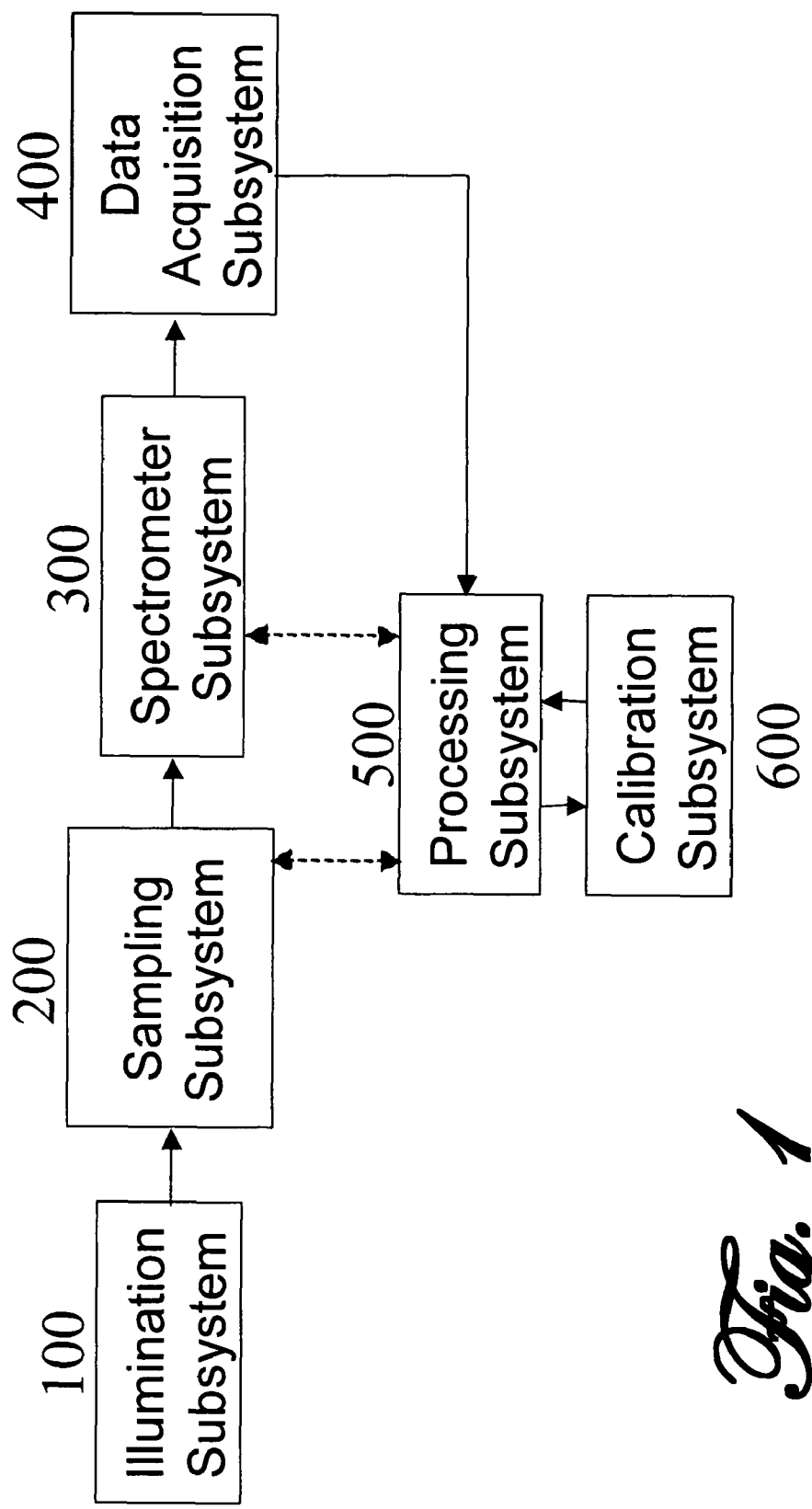
FIG. 1 is a schematic depiction of a system according to the present invention.

Detailed embodiments of the present invention are disclosed herein. However, it is to be understood that the disclosed embodiments are merely exemplary of the present invention which can be embodied in various systems. Therefore, specific details disclosed herein are not to be interpreted as limiting, but rather as a basis for the claims and as a representative basis for teaching one of skill in the art to variously practice the invention.

Various methods for reducing the influence of non-analyte spectral effects inherently present in the sample have been proposed; an understanding of those can aid in appreciation of the present invention. In US 2003/0216627 A1, incorporated herein by reference, Lorentz et al. disclose a measurement site dependent preprocessing method for robust calibration and prediction of analytes in humans. The method refers to tissue heterogeneity caused by site-to-site variations, differences between people, differences between instruments and physiological drift over time. They do not disclose topical or otherwise introduced foreign interferents that might be present on or within the sample. Furthermore, the method requires the transformation of measurements prior to application of the multivariate calibration model using a basis set of measurements acquired at the same measurement site. The present invention does not require transformation of measurements nor does it involve a basis set of measurements at the measurement site to derive such a transformation.

In U.S. Pat. No. 6,862,534 B2, incorporated herein by reference, Sterling et al. disclose a method for determining an analyte concentration from an absorbance spectrum. The method involves acquiring a spectrum, performing a baseline correction and/or scaling of the spectrum, and subtracting the signal of a substance from the measured absorbance spectrum. The term substance is described in the context of other chemical components that are inherently present in the sample. Foreign interferents that might be present on or within the sample are not disclosed. Furthermore, no embodiments of the present invention involve baseline shifts or corrections, scaling steps, or subtraction of a substances signal from the measurement.

In U.S. Pat. Nos. 6,341,257 B1 and 6,711,503 B2, incorporated herein by reference, Haaland discloses hybrid least squares multivariate analysis methods. Haaland et al. also describe "new prediction-augmented classical least-squares (PACLS) methods: application to unmodeled interferents" in *Applied Spectroscopy*, vol. 54(9), 2000, which is closely related to U.S. Pat. Nos. 6,341,257 B1 and 6,711,503 B2. All of the embodiments described require the use of an initial multivariate calibration to obtain a set of measurement errors followed by a second multivariate calibration generated from the measurement errors of the initial model. U.S. Pat. No. 6,711,503 B2 discloses the addition of one or more spectral shapes not represented in the initial calibration model to the spectral set (thereby generating a hybrid set of spectra) prior to the generation of the second multivariate calibration model using the measurement errors. In these embodiments, the analyte concentrations of future measurements would be determined using the initial calibration with a measurement error correction from the second calibration. The present invention does not require the use of a second multivariate calibration derived from measurement errors.

In U.S. Pat. No. 6,697,654 B2, incorporated herein by reference, Lorentz et al. disclose a method for targeted interference subtraction applied to near-infrared measurement of analytes. All of the disclosed methods involve the use of an "interference model" to estimate the signal of the interferent in a measurement. The estimated signal is then subtracted from the measurement to obtain a corrected measurement that is then used with a multivariate calibration model to determine the analyte concentration. The present invention does not require quantitative estimation of an interferent's contribution to a measurement, nor that the contribution be subtracted from the measurement prior to application of the multivariate calibration model.

In U.S. Pat. No. 6,512,937 B2, incorporated herein by reference, Blank et al. disclose a multi-tier method of developing localized calibration models for noninvasive blood analyte prediction. All of the disclosed embodiments involve classifying the data in a calibration set into multiple classes in at least one tier based on subject demographics and spectral measurements. At least one feature of each spectrum within each class and within each tier is then extracted for further classification. A multivariate calibration model is then developed for each group of spectra resulting from the tiered classification/extraction/classification scheme. The present invention does not classify data based on subject demographics or subject dependent properties nor does it require multi-tiered classification schemes. Foreign interferents present on or within the sample are not addressed in Blank.

In U.S. Pat. No. 6,405,065 B1, incorporated herein by reference, Malin et al. disclose noninvasive in vivo tissue classification using near-infrared measurements. The disclosed embodiments require either visual inspection of the near-infrared measurement followed by enhancement to correct for scatter, a set of spectral measurements acquired from the same measurement site to isolate tissue specific variations using a decomposition of said set to isolate the desired spectral features, or transgenic mice. The present invention does not require any of the above-described steps. Malin's teaching relates to classification based on physiological differences; foreign interferents are not disclosed.

In U.S. Pat. No. 6,280,381 B1, incorporated herein by reference, Malin et al. disclose an intelligent system for noninvasive blood analyte prediction. The invention discloses a hierarchical architecture pattern classification system to adapt a multivariate calibration model to the structural properties and physiological state as manifested in the absorbance spectrum to be measured. All of the disclosed embodiments involve the generation of a classification engine that groups similar subjects together such that a calibration model can be generated for each group. The resulting calibration models are meant to reduce the effects of inter-subject difference in optical properties and tissue structure. Foreign interferents and substances introduced to the sample are not disclosed. The present invention does not classify either the calibration data or future measurements based on subjects or subject properties.

Shao et al, describe "Immune algorithms in analytical chemistry" in *Trends in Analytical Chemistry*, Vol. 22(2), 2003, incorporated herein by reference. They disclose an algorithmic approach to reduce the effects of antigens (multicomponent analytical signals) on an experimental measurement using antigens (standard signals of assumed components) by iteratively subtracting the antigen signal and applying a calibration until the analyte measurement stabilizes. The present invention does not require recursive subtraction of signals from measurements. Further, the disclosed applications of the method are chromatography, photo-acoustic measurements, nuclear magnetic resonance signals, and two-dimensional chromatography. Infrared and near-infrared spectroscopies are not discussed.

Presently, alcohol measurements in humans require a bodily fluid (typically blood, saliva, sweat, breath, or urine) to be acquired from the subject in order to facilitate the alcohol measurement. These samples expose the test administrator to biohazards and generally require some measure of cooperation from the subject. Given the often-punitive nature of alcohol measurements (e.g. DUI enforcement), the subject can be motivated to be uncooperative and thereby compound the biohazard risk to all parties involved. U.S. patent application Ser. No. 10/852,415, entitled "Noninvasive determination of alcohol in tissue," filed May 24, 2004 and incorporated herein by reference, discloses a method for the noninvasive measurement of alcohol based on spectroscopic techniques that provides an alternative to the current blood, breath, urine, saliva, and transdermal methods. The noninvasive alcohol concentration of the subject is obtained using the absorption or reflection spectra of the subject's tissue. No bodily fluid is required for the noninvasive measurement, thereby eliminating biohazard concerns. Furthermore, only passive contact is required between the subject and the noninvasive device, which greatly reduces the opportunity for the subject to be uncooperative.

However, a potential problem encountered in non-invasive measurements is the possible presence of foreign interferents that can adversely influence the noninvasive measurement. For the present invention, the term "interferent" or "interference" means a foreign substance that has been introduced to the sample being measured. This includes, for example, topically applied medications or products such as perfumes, colognes, lotions, creams, topical steroids, etc. as well as medications, drugs, or substances introduced via other means (oral ingestion or injection). The term "interferent" or "interference" is not intended to include naturally present substances at their normal concentrations. For example, in non-invasive tissue measurements, collagen is naturally present in tissue within a certain range of physiological concentrations. As such, it is not an interferent for the purposes of this invention unless something (e.g. a collagen injection) has artificially increased its concentration.

It is recognized that interferents can also influence measurements of analytes other than alcohol and in a variety of sample types. For example, measurements of glucose, urea, byproducts of alcohol metabolism, and substances of abuse will also benefit from interferent detection/identification/mitigation methods. For the purposes of this invention, the term "alcohol byproducts" includes the adducts and byproducts of the metabolism of alcohol by the body including, but not limited to, acetone, acetaldehyde, and acetic acid. The term "substances of abuse" refers to, but is not limited to, THC (Tetrahydrocannabinol/marijuana), cocaine, M-AMP (methamphetamine), OPI (morphine and heroin), OxyContin, Oxycodone, and PCP (phencyclidine). It is worthy to note that in some situations, the chemical identity of the interferent and analyte can be the same. For example, topically applied alcohol is a recognized interferent when measuring tissue alcohol. While the remainder of the disclosure largely focuses on noninvasive in vivo alcohol measurements, it is used for demonstrative purposes and should not be construed as limiting to the invention.

The invention is described in terms of "signals", described in some of the examples as absorbance or other spectroscopic measurements. Signals can comprise any measurement obtained concerning a spectroscopic measurement of a sample or change in a sample, e.g., absorbance, reflectance, intensity of light returned, fluorescence, transmission, Raman spectra, in each case comprising information about the sample or change in the sample acquired at more than one detection wavelength. "Spectrum" and "spectra" are also used herein to refer to signals. The invention also concerns analyte properties, where an analyte property can include, as examples, analyte concentration, presence of an analyte, identity of an analyte, change or rate of change in analyte concentration or other property of an analyte, form of an analyte (e.g., oxygenation), temperature, activity, and conformation. Some embodiments make use of a multivariate calibration model, where such a model can be anything that relates a signal to the desired property, e.g., PLS models, linear regression models, Beer's law models. The terms "mitigate" or "interferent mitigation" can comprise any step or group of steps designed to reduce or alter the effects of an interferent or interferents on any of the spectral measurement, analyte measurement, or actions of the user. Advances in optical materials and multivariate algorithms over the last several decades have created the potential for expanding spectroscopic measurements into new areas of interest. One such area is the noninvasive measurement of alcohol in humans. As used herein, the term "alcohol" includes, but is not limited to, one or more of the following: ethanol, ethyl alcohol, methanol, methyl alcohol, propanol, propyl alcohol, isopropyl alcohol, glycol, ethylene glycol, or any equivalent term such as "wood grain alcohol".

The following detailed description should be read with reference to the drawings. The drawings, which are not necessarily to scale, depict illustrative embodiments that are not intended to limit the scope of the invention. For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

A sample such as human tissue can be a complex matrix of materials with differing refractive indices and absorption properties. Alcohol can be one material in such a matrix, and is used as an example in some of the illustrative embodiments. However, the illustration of embodiments herein that relies on alcohol should not be considered limiting, as the present invention is suitable for use in connection with many analytes. Primarily for purposes of illustration, not limitation, the present invention is described with particular reference to noninvasive alcohol measurements.

Figure 2:
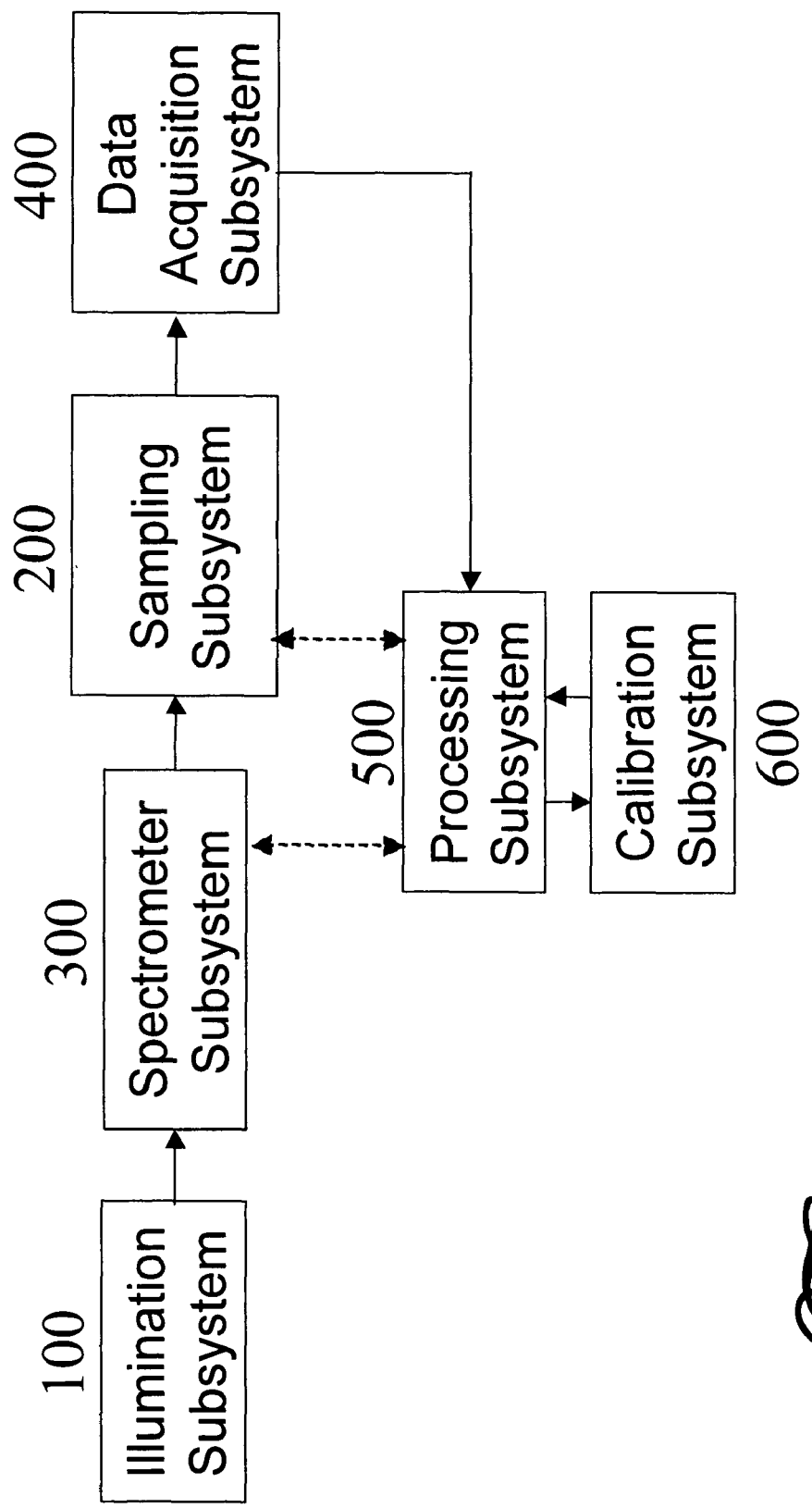
FIG. 2 is a schematic depiction of a system according to the present invention.

Some embodiments of the present invention comprise an apparatus for measuring a sample or portion of a sample. As an example of such an apparatus, FIG. 1 shows a schematic depiction of a non-invasive monitor. The overall system can be viewed for discussion purposes as comprising six subsystems; those skilled in the art will appreciate other subdivisions of the functionality disclosed. The subsystems comprise an illumination subsystem 100, a sampling subsystem 200, a spectrometer subsystem 300, a data acquisition subsystem 400, a processing subsystem 500, and a calibration subsystem 600. The subsystems can be designed and integrated in order to achieve a desirable signal-to-noise ratio and performance. FIG. 2 is a schematic depiction of an alternative arrangement of the elements shown in FIG. 1: the spectrometer subsystem and sampling subsystem have been exchanged relative to the system of FIG. 1. Those skilled in the art will appreciate the effect of interchanging elements and subsystems in an optical path. The subsequent discussion assumes the arrangement of FIG. 1 for simplicity, but is not meant to preclude alternative arrangements of the subsystems.

Figure 3:
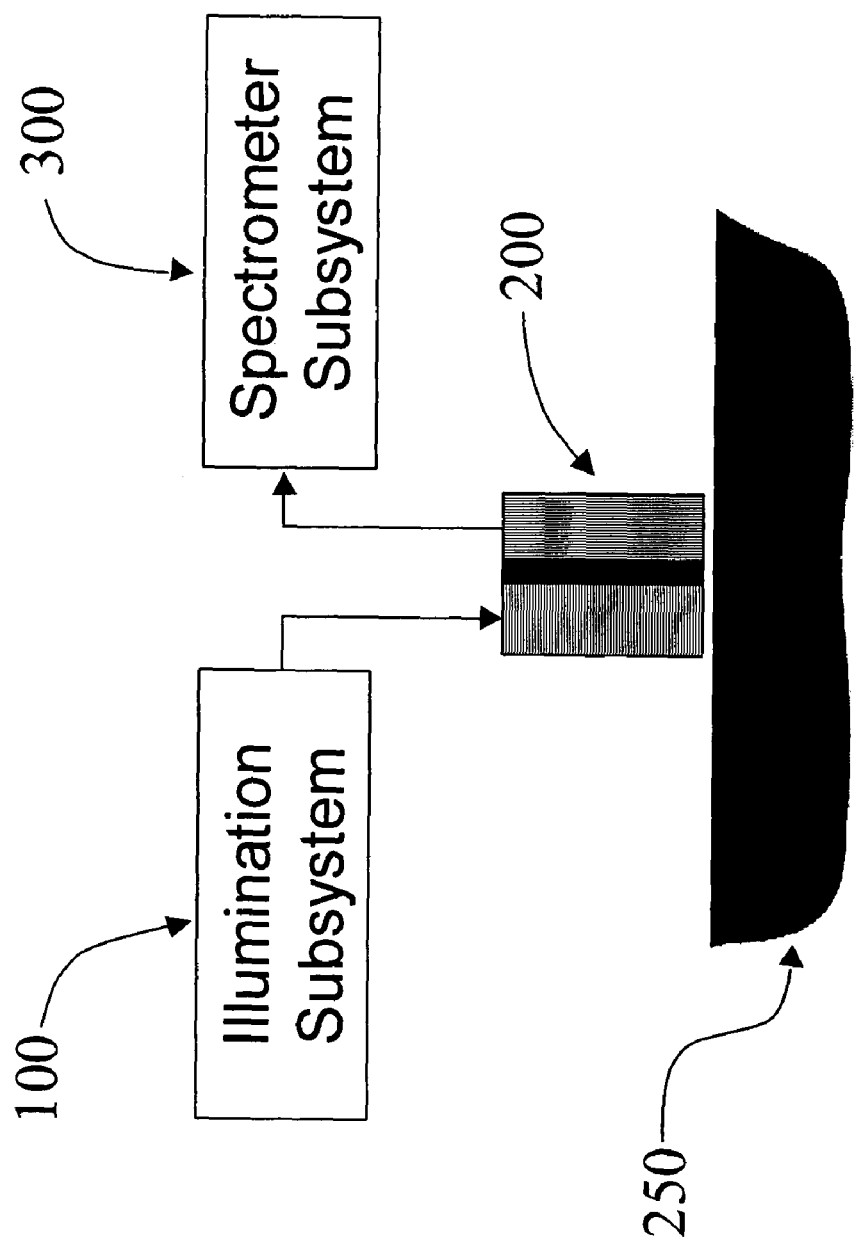
FIG. 3 is a schematic depiction of a system that measures the sample in reflectance.
Figure 4:
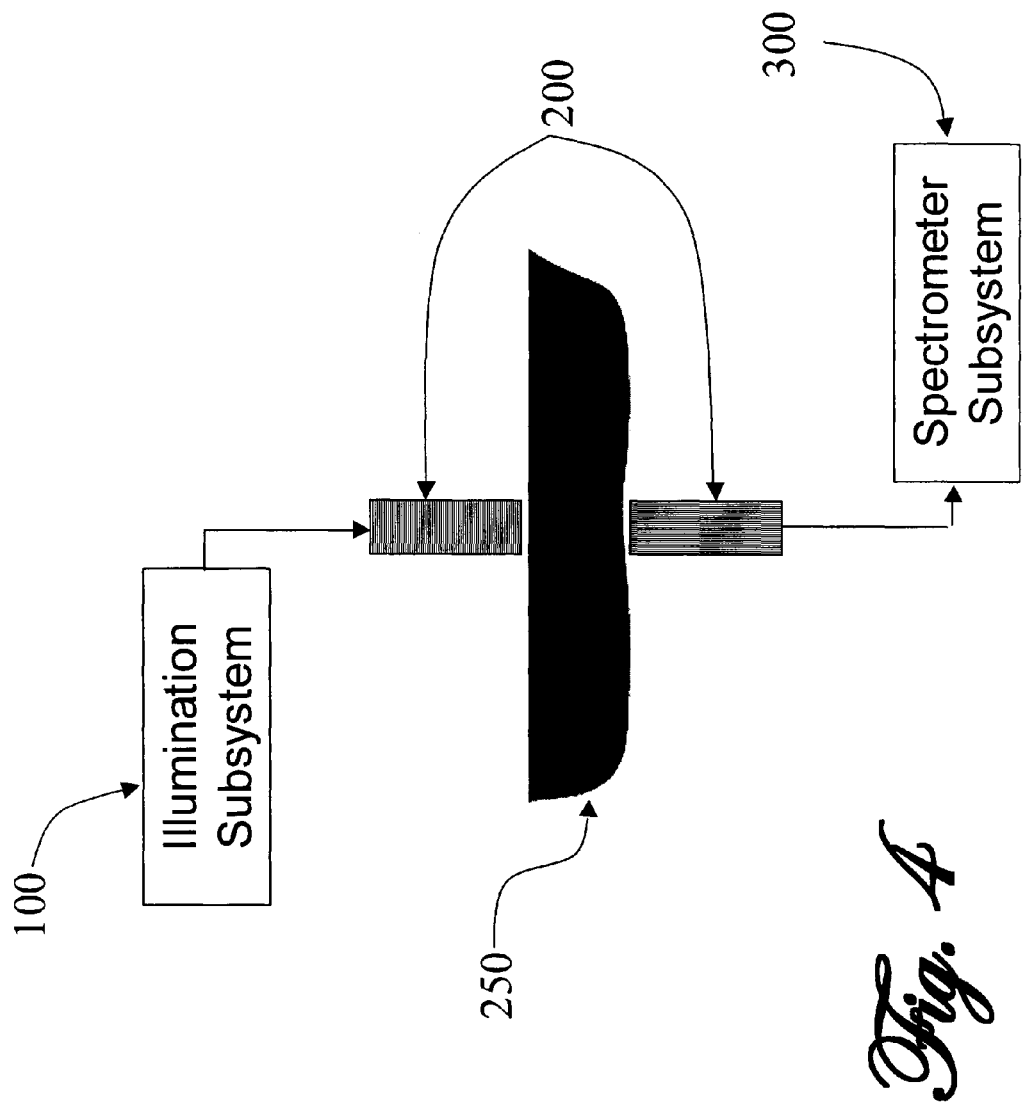
FIG. 4 is a schematic depiction of a system that measures the sample in transmission.

An area or portion of a sample can be selected as the point or portion of analysis for the sampling subsystem. In the case of noninvasive tissue measurements, this area can comprise the skin surface on the finger, earlobe, forearm, or any other skin surface. Embodiments of the sampling subsystem 200 can be such that light is introduced and collected from the sample 250 in either reflectance or transmission geometries (shown in FIGS. 3 and 4, respectively). One example embodiment of the sampling subsystem 200 measures the underside of the forearm using reflectance geometry, and will be used to describe various embodiments of the present invention.

As illustrated in FIG. 1, the sampling subsystem 200 introduces radiation generated by the illumination subsystem 100 to the sample and collects portions of the radiation not absorbed by the sample, and communicates that radiation to a spectrometer subsystem 300 for measurement. FIGS. 5 through 10 depict elements of a sampling subsystem 200.

Figure 5:
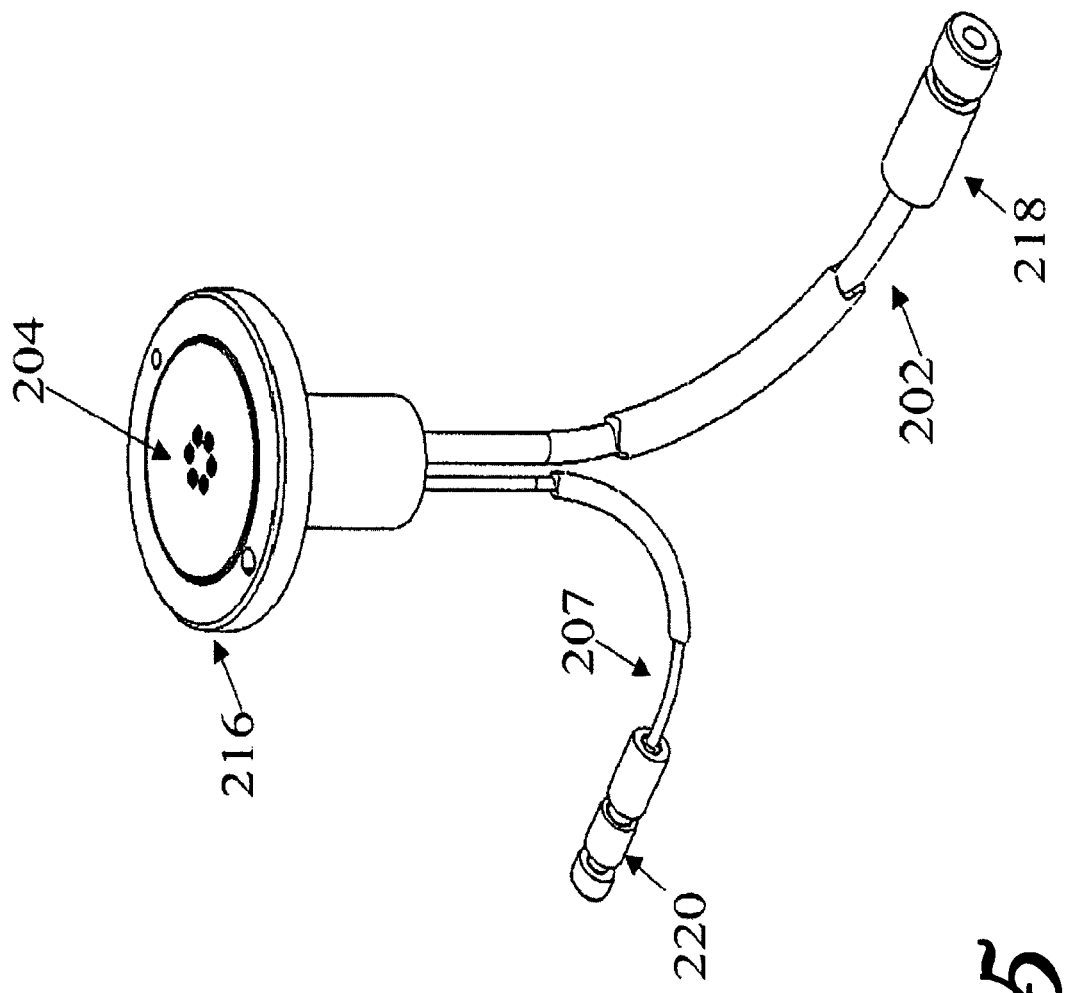
FIG. 5 is a perspective view of elements of an example tissue sampling subsystem.

Referring to FIG. 5, the sampling subsystem 200 has an optical input 202, a sampling surface 204 which forms an interface 206 that interrogates the sample and an optical output 207. A device that thermostats the sampling subsystem/sample interface can be included. An index matching fluid can be used to improve the optical interface between the sample and sampling subsystem. See, e.g., U.S. Pat. No. 6,152,876 issued to Robinson et al., incorporated herein by reference. In some measurement applications, the index matching fluid can be considered an interferent that warrants application of a mitigation method according to the present invention.

Figure 6:
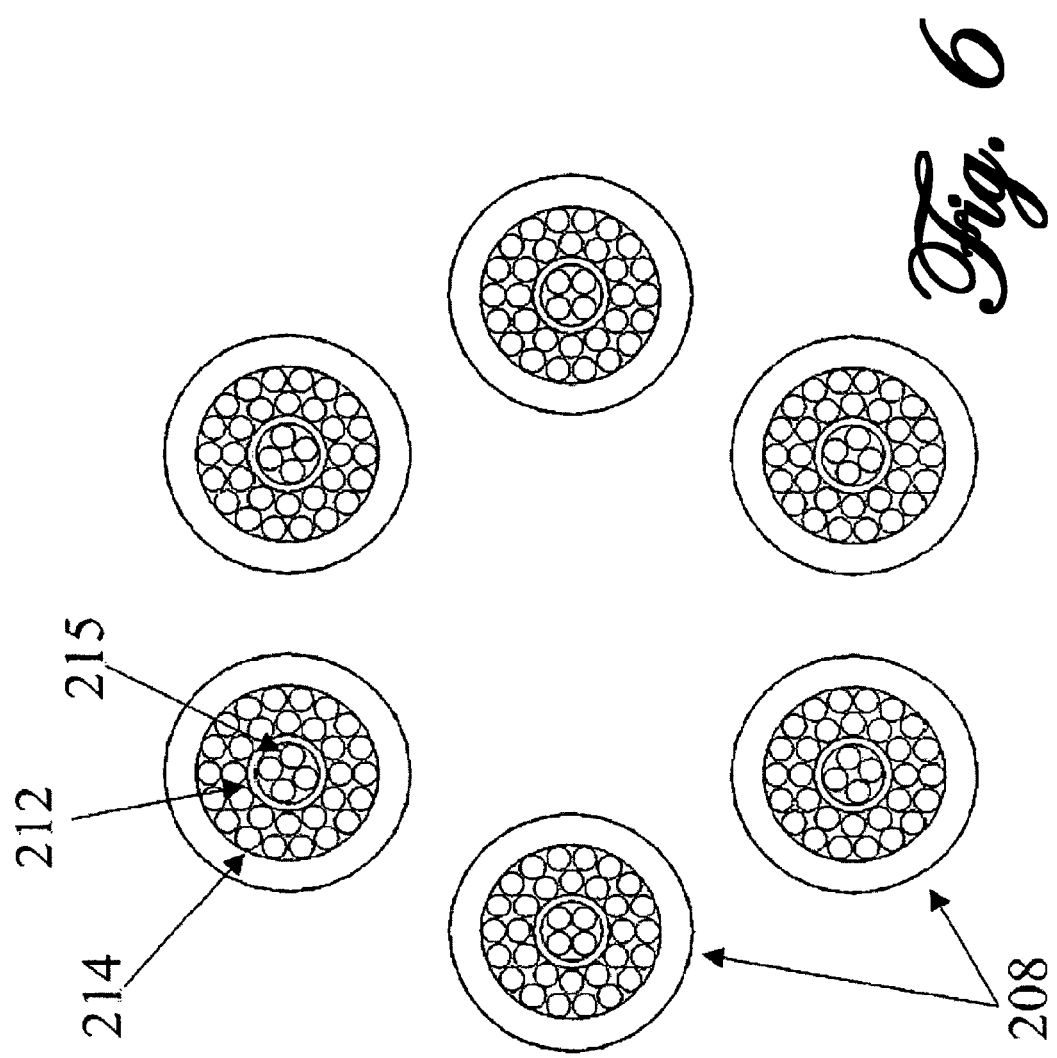
FIG. 6 is a plan view of the sampling surface of the tissue sampling subsystem, showing an example arrangement of input and output optical fiber ends.

The optical input 202 of the sampling subsystem 200 receives radiation from the illumination subsystem 100 (e.g., light exiting a light pipe or other means for coupling light) and transfers that radiation to the interface 206. As an example, the optical input can comprise a bundle of optical fibers arranged in a geometric pattern that collects an appropriate amount of light from the illumination subsystem. The sampling head 216 comprises a sampling surface 204, which can be polished flat to encourage formation of a good interface with the sample and prevent accumulation of interferents on the sampling head surface. FIG. 6 depicts one example arrangement. The plan view depicts the ends of the input and output fibers in a geometry at the sampling surface including six clusters 208 arranged in a circular pattern. Each cluster comprises four central output fibers 212, which collect diffusely reflected light from the sample. Around each grouping of four central output fibers 212 is a cylinder of material 215, which can ensure a gap (e.g., about 100 μm) between the edges of the central output fibers 212 and the inner ring of input fibers 214. A gap between input and output fibers can be important to measuring certain analytes such as alcohol. As shown in FIG. 30, two concentric rings of input fibers 214 can be arranged around the cylinder of material 215. As shown in one example embodiment, 32 input fibers surround four output fibers.

Figure 7:
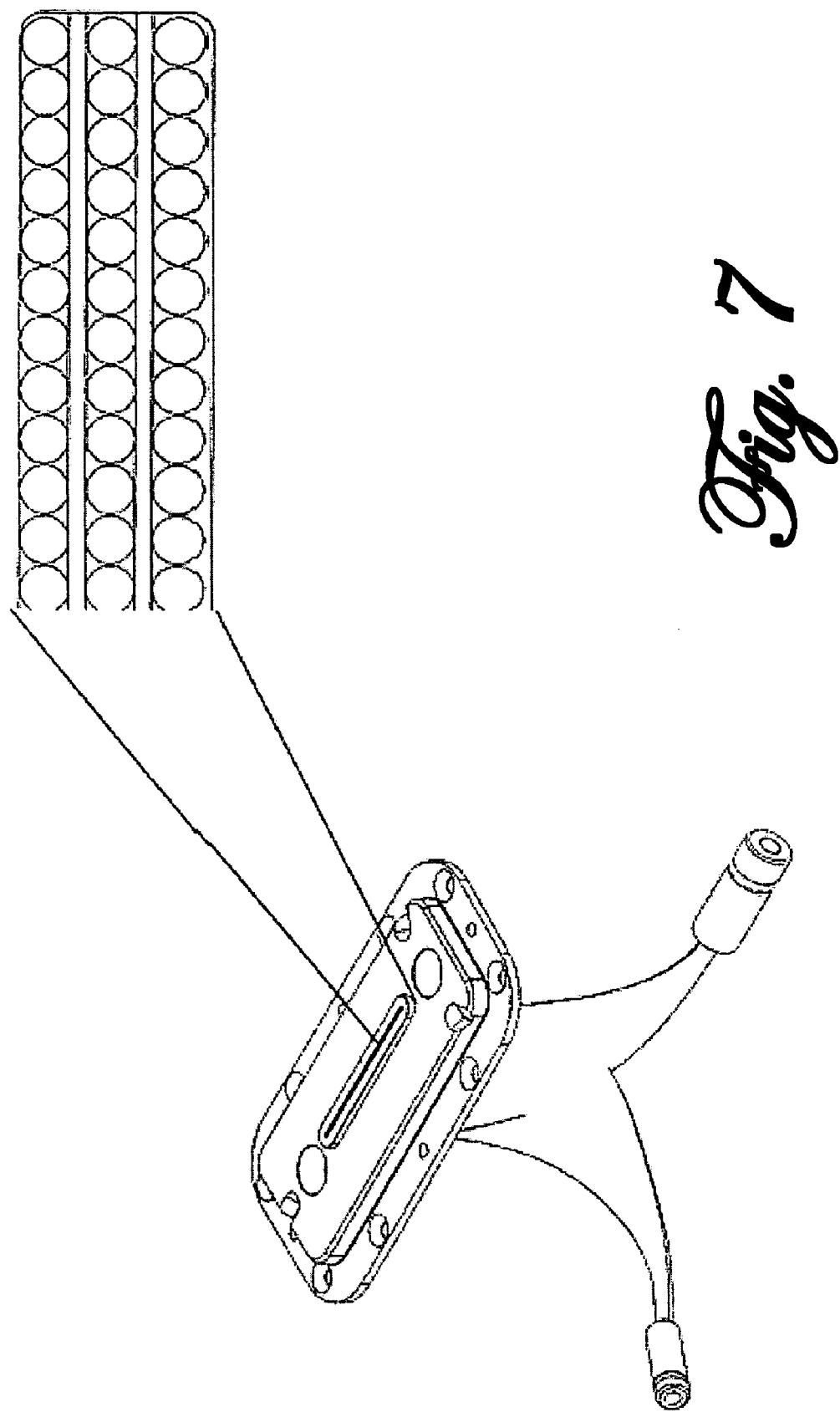
FIG. 7 is an alternative embodiment of the sampling surface of the tissue sampling subsystem.

FIG. 7 demonstrates another arrangement of fibers in a sampling subsystem. In this embodiment, the illumination and collection fiber optics are arranged in a linear geometry. Each row can be for illumination or for light collection, and can be of any length suitable to achieve sufficient signal to noise. In addition, the number of rows can be 2 or more to alter the physical area covered by the sampling subsystem. The total number of illumination fibers can depend on the physical size of emissive area of the light source and the diameter of each fiber. Multiple light sources can be used in the illumination subsystem 100 to increase the number of illumination fibers. The number of collection fibers can depend on the area of the interface to the spectrometer subsystem 300. If the number of collection fibers results in an area larger than the spectrometer subsystem 300 interface allows, a light pipe or other homogenizer followed by an aperture can be used to reduce the size of the output area of the sampling subsystem. The light pipe or other homogenizer can encourage each collection fiber to contribute substantially equally to the light that passes through the aperture.

Figure 8:
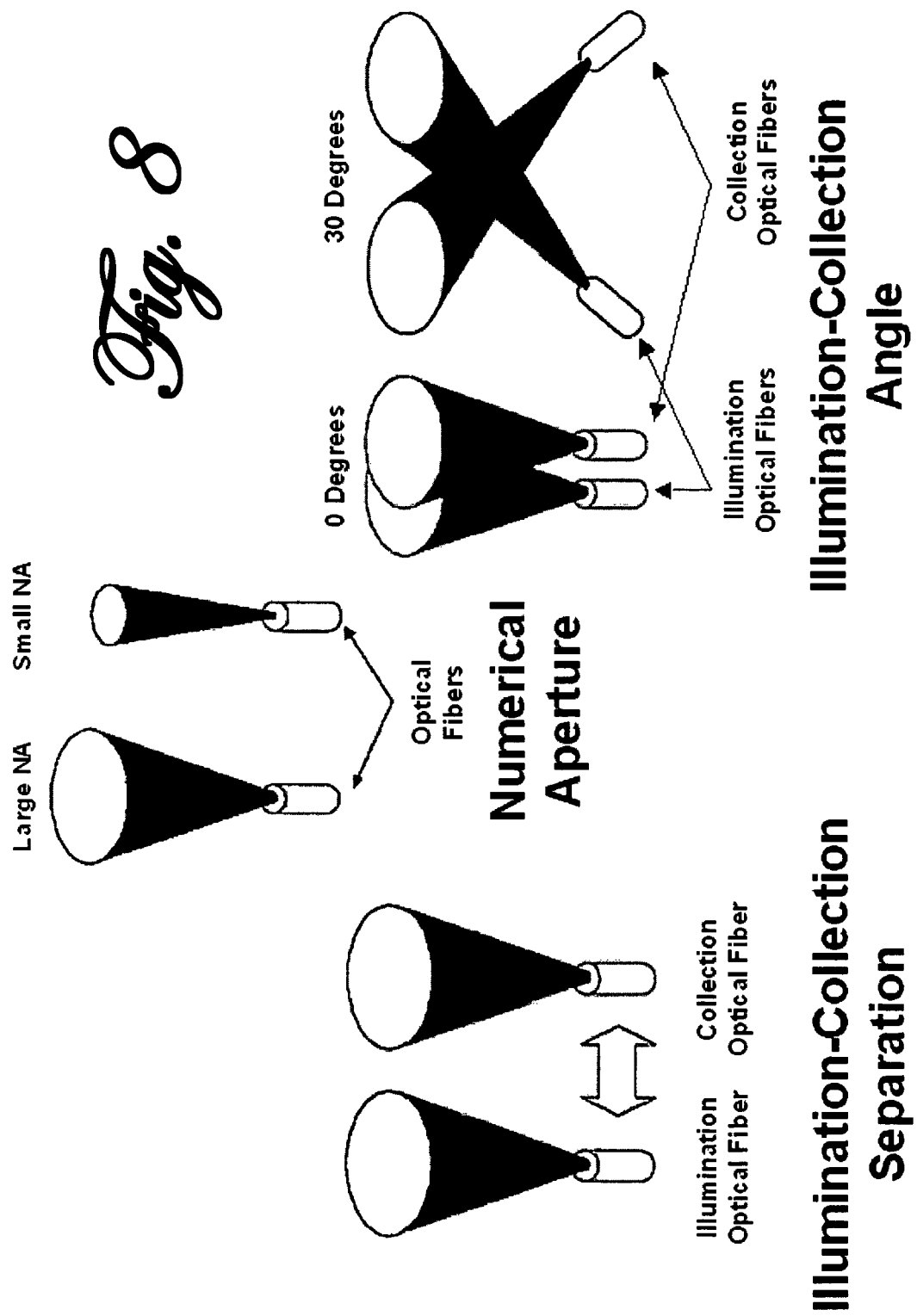
FIG. 8 depicts the various aspects of a sampler orientation.
Figure 9:
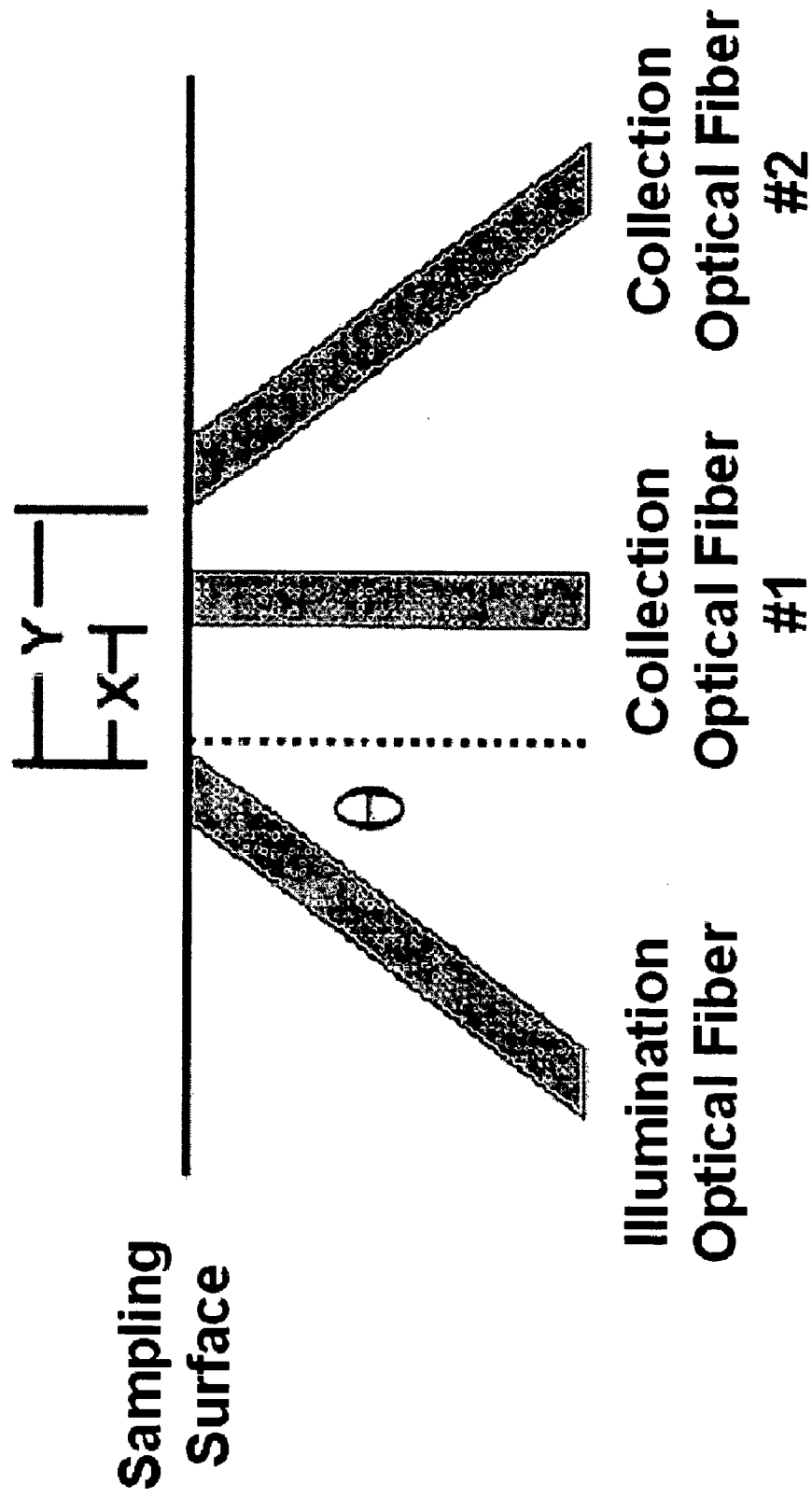
FIG. 9 is a diagramed view of a two-channel sampling subsystem.

The sampling subsystem can use one or more channels, where a channel refers to a specific orientation of the illumination and collection fibers. An orientation is defined by the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 8 is a diagram of parameters that form an orientation. Multiple channels can be used in conjunction, either simultaneously or sequentially, to improve analyte measurements. FIG. 9 is a diagram of a two channel sampling subsystem. Each channel provides a measurement of the sample from a different perspective, e.g., response of the sample along different paths through the sample. The second perspective can provide additional spectroscopic information that helps to decouple the signals due to scattering and absorption. Referring to FIG. 9, the group of fibers (1 source, 1 receiver #1, and 1 receiver #2 in this example) can be replicated 1 to N times in order to increase the sampler area and improve optical efficiency. Each of the fibers can have a different numerical aperture and angle (θ). The distances between fibers, X and Y, determine the source receiver separation. Furthermore, an additional source channel can be added that creates a 4-channel sampling subsystem. Those skilled in the art will appreciate many variations contemplated by the present invention and illustrated by the examples discussed.

Figure 10:
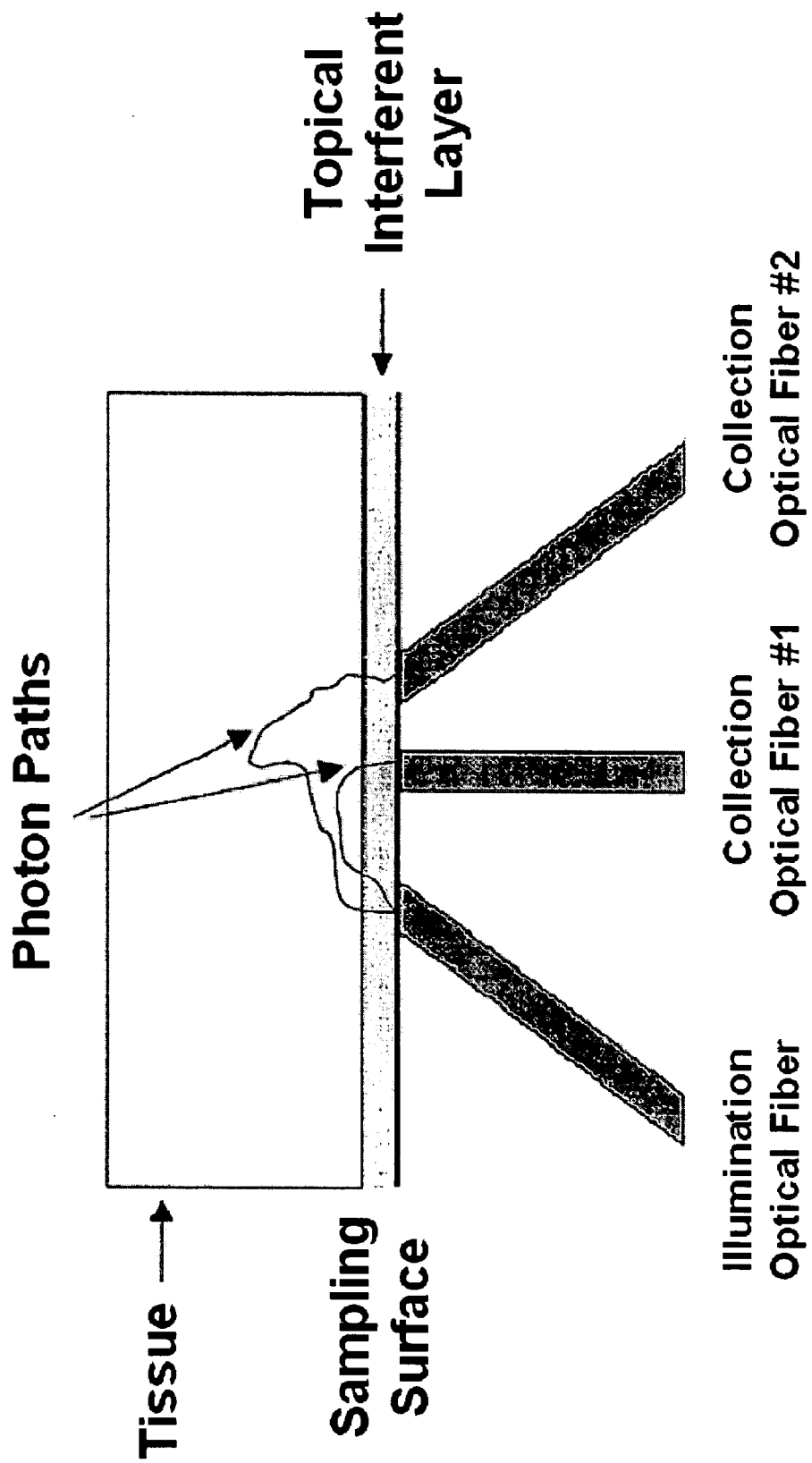
FIG. 10 is a diagramed view of the interface between the sampling surface and the tissue when topical interferents are present on the tissue.

A multiple channel sampling subsystem can improve detection and mitigation of topical interferents, such as skin lotion, present on the sample. FIG. 10 is a diagram of a multiple channel sampling subsystem in the presence of a topical interferent. FIG. 10 shows the sampling subsystem/sample interface, a layer of topical interferent, and the tissue. In this example, the interferent's contribution to the signal of each channel is substantially similar since the light from both channels passes through the interferent-containing layer twice. The tissue signal, however, will be different in the two channels due to the different path. This allows the potential to decouple the common topical interferent signal, present in both channels, from the tissue signal. If an interferent is localized in a specific layer (e.g. a topical interferent in the epidermis), a combination of channels in the sampling subsystem 200 can be used to exclude or reduce the signal from that layer, and therefore aid in mitigating the effects of the interferent on the analyte measurement.

The optical and mechanical design of the sampling subsystem can be such that it has reduced susceptibility to interferents and interferent contamination. For example, the materials used to fabricate the sampling subsystem (which can contact the sample) can be chosen such that they are immune to certain classes of interferents. For example, as Teflon is known to absorb and hold water, it might be avoided in sampling subsystems where water contamination could occur. Furthermore, the optical design can be such that contact between the sensor element and sample is not necessary, thereby prohibiting contamination of the sensor by an interferent-containing sample.

In addition to the use of optical fibers, the sampling subsystem can use a fiberless optical arrangement that places a pattern of input and output areas on the sample surface. In some embodiments, the input and output elements of the sampling subsystem can be comprised of a lens system. In an example embodiment, the input element and output element comprise a single lens system that is utilized for both input of light from the energy source and the collection of both specularly and diffusely reflected light from the sample. Alternatively, the input element and output element can comprise two lens systems, placed on opposing sides of an analyte-containing sample, wherein light from the energy source is transmitted to the input element and onto the sample, and light transmitted through the analyte-containing sample then passes through the output element to the spectrum analyzer. Proper masking of a fiberless optical tissue sampling interface ensures that the input light travels a minimum distance in the tissue and contains valid attribute information.

In either of the apparatus orientations shown in FIGS. 1 and 2, a data acquisition subsystem 400 can convert the light collected from either the sampling or spectrometer subsystems to a digital representation of the spectrum of light acquired from the sample (e.g. intensity or absorbance versus wavelength or frequency). In the context of noninvasive alcohol measurements, each measured spectrum can be used in combination with a multivariate calibration model to determine the alcohol concentration in the sample (the tissue). The multivariate calibration model can empirically relate known alcohol concentrations in a set of calibration samples to the measured spectral variations obtained from the calibration samples. This relationship can then be applied to subsequent measurements. In an example embodiment, a multivariate calibration model is derived using the partial least squares (PLS) algorithm and method, although other multivariate techniques can be employed.

Figure 11:
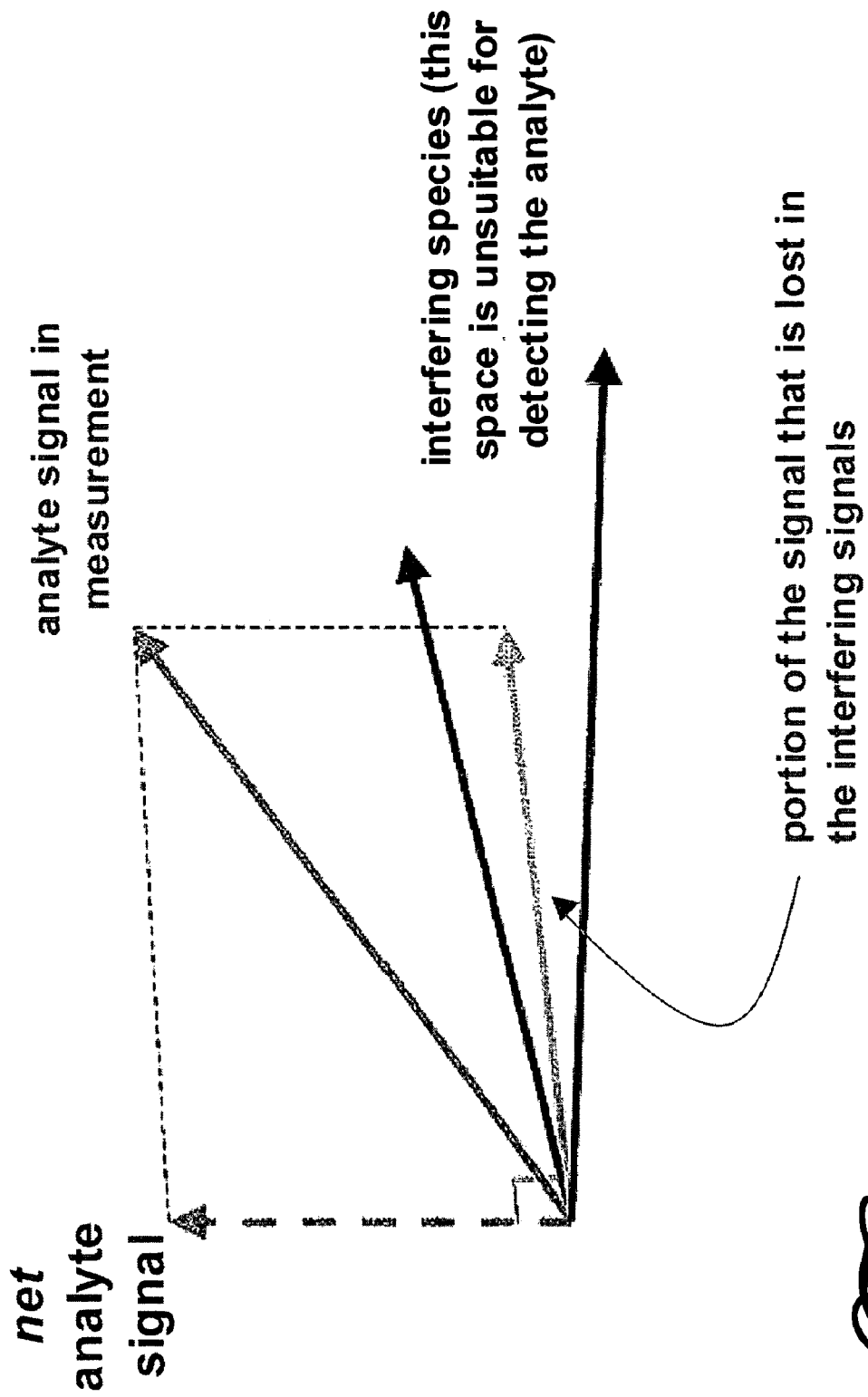
FIG. 11 is a graphical depiction of the concept of net attribute signal in a three-component system.

The PLS algorithm uses the calibration data to determine the portion of a spectrum that is directly related to the analyte while substantially independent of other sources of spectral variation. The net analyte signal (NAS) is a metric that is related to the amount of independent analyte signal. For each non-analyte source of spectral variation a fraction of the analyte signal is consumed, thereby reducing the remaining net analyte signal. FIG. 11 is a graphical representation of the net analyte signal in a three dimensional system. Two of the dimensions represent the interfering signals and the third is the signal of the analyte or interest. The multivariate algorithm determines the portion of the analyte signal that is effectively orthogonal to the interfering signals and uses only that portion in forming the empirical relationship between spectral measurements and analyte concentrations.

One characteristic of multivariate methods is that the resulting calibration model is generally orthogonal only to sources of spectral variation that were present in the set of calibration measurements. In other words, if a foreign interferent that was not present in the calibration data is present in a future sample, the foreign interferent can have an unknown, potentially significant detrimental effect on the analyte measurement. Inclusion of all possible interferents in the calibration data can address this situation. While this can be feasible for simple systems with a small number of interferents, it can be impractical for complex systems such as noninvasive measurements of tissue for two reasons. First, the number of calibration measurements would need to be very large, which could be prohibitively expensive in terms of time and resources. Second, each interferent can consume some of the net analyte signal, which can result in a calibration model that exhibits poor precision due to the small amount of remaining analyte signal.

The present invention includes apparatuses and methods for mitigating the effects of foreign interferents on analyte measurements. The present invention comprises several interferent mitigation steps. Examples include sample cleaning procedures, detection of the presence of interferents, determination of the identity of interferents, and modification or selection of a multivariate calibration model to mitigate the effects of one or more interferents on analyte measurements. The interferent mitigation steps of the present invention can be applied individually, and in some embodiments can be applied in combination. Those skilled in the art will appreciate other combinations; the example embodiments should not be construed as limiting to the invention.

One mitigation method comprises removing the interferent, prior to the measurement, by cleaning the sample. For example, in noninvasive alcohol measurements a disposable isopropyl alcohol wipe can be used on the selected tissue site prior to the measurement. A cleaning procedure can be initiated based upon a user's suspicion of an interferent, or as part of a pre-measurement standard procedure. Furthermore, the cleaning step can require the use of more than one cleaning agent (either in the same solution, or applied sequentially). For example, cologne or perfume might be cleaned with one cleaning agent and grease might be cleaned with a different cleaning agent. If both cologne and grease are present, both cleaning agents might be necessary. Alternatively, a "complete" cleaning agent can include all individual cleaning agents necessary to clean the majority of potential interferences. Any cleaning methodology can be combined with other mitigation steps to develop a more comprehensive mitigation method.

The cleaning process can introduce an interferent (the cleaning agent itself) to the sample. This can be an acceptable consequence of cleaning as it can effectively condense a large number of potential interferents to those present in the cleaning agents (whose identities can generally be known). For example, the use of an isopropyl alcohol wipe can introduce isopropyl alcohol to the sample surface. The effects of the introduced interferent on the measurement can be negligible, with some cleaning agents and in the measurement of some analyte properties, and can be ignored. When the cleaning agent can not be ignored, it can be accounted for in the data used to create the multivariate calibration model. The applied cleaning procedure can dictate the selection of a specific multivariate calibration from a library of calibrations. For example, in the noninvasive measurement of ethyl alcohol in tissue, the application of an isopropyl alcohol cleaning procedure to the tissue surface can result in the selection of an ethyl alcohol multivariate calibration that incorporates the interfering effects of isopropyl alcohol.

A mitigation method can also involve detection of the presence of interferents by analyzing a spectral measurement for abnormal spectral signatures. The analysis can be performed using a variety of means such as comparison of the spectrum to a reference library of spectra that contain various interferents, examination of the residuals of a principal components analysis (PCA) or the residuals obtained from the application of the multivariate calibration model, or metrics such as the Mahalanobis Distance and spectral F-ratio (Q-Statistic). Furthermore, the analyte measurement itself can be a means for detecting the presence of interferents. For example, an analyte measurement that is clearly outside the range of physically possible concentrations (e.g. an in vivo alcohol concentration that would clearly be lethal, or, if multiple measurements are made, results that vary in a manner not consistent with human tissue) can be indicative of one or more interferents corrupting the measurement. Other methods such as classification algorithms and neural networks can also be used to detect the presence of interferents.

The identity of the interferent or interferents does not need to be determined if knowledge of the presence of an interferent (and not the identity) can be sufficient information to specify a course of action. For example, a measurement administrator can disqualify a sample and/or initiate a procedure to clean an unknown interferent or interferents from the sample, at which point new spectra from the sample can be obtained.

Figure 12:
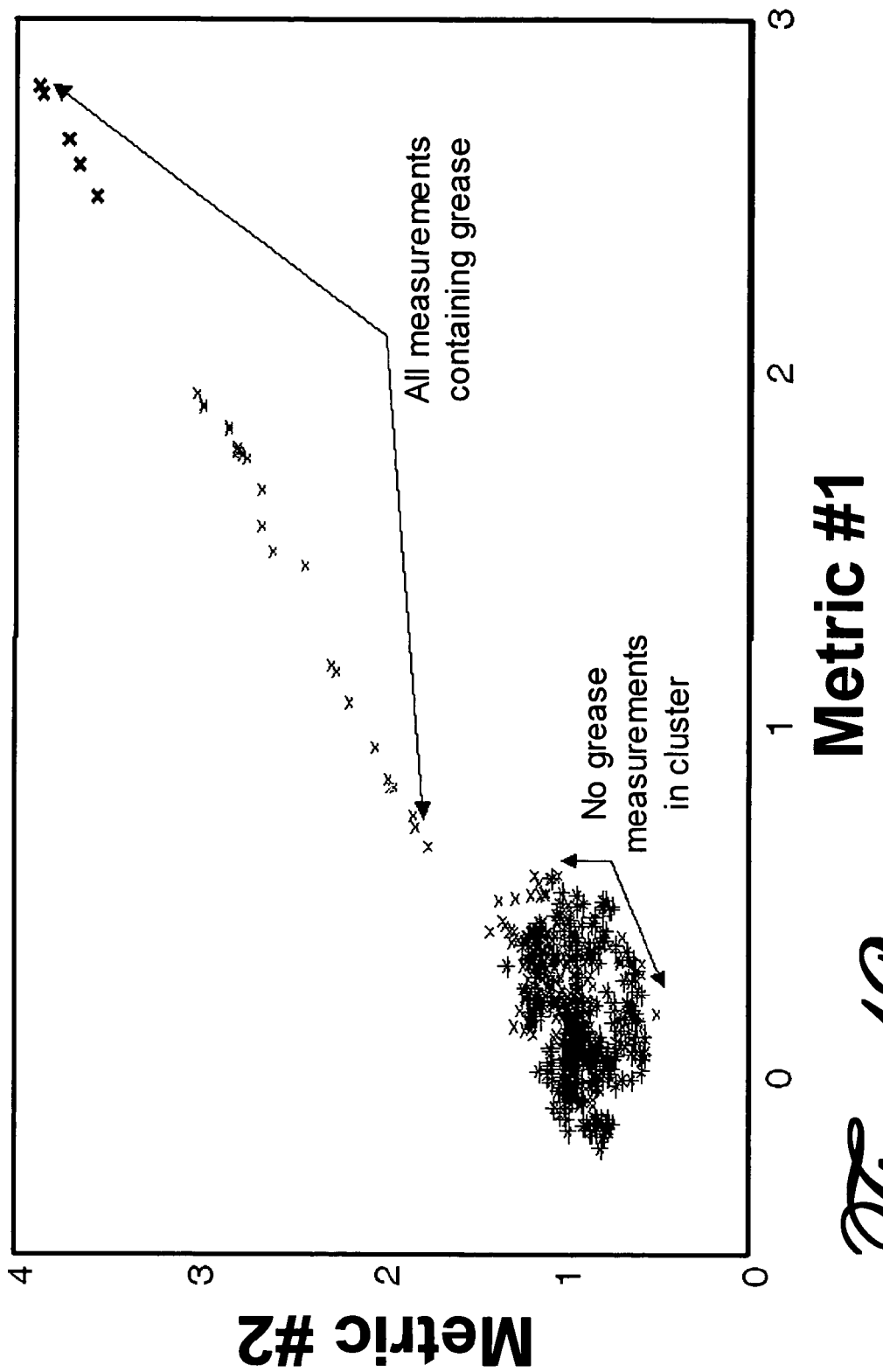
FIG. 12 demonstrates the effectiveness of multivariate calibration outlier metrics for detecting the presence of topical interferents.

Clinical results obtained from an embodiment of an interferent detection step are shown in FIG. 12, which shows outlier metric values obtained from noninvasive measurements of in vivo human tissue acquired using an apparatus similar to that described in the present invention. All of the large metric values (clearly separated from the majority of the points) correspond to measurements where grease had been intentionally applied to the subject's skin. While these metrics do not specifically identify the cause of the outlier, they do indicate that the associated attribute measurement is suspect. An out of bound outlier metric value (a value greater or less than a fixed threshold, for example) can be used to trigger a fixed response such as a repeat of the measurement, application of an alternative multivariate calibration model, or a sampling site cleaning procedure. Examples of outlier metrics are discussed in U.S. Patent Application 20040204868, "Reduction of errors in non-invasive tissue sampling," filed Apr. 9, 2003, incorporated herein by reference.

The step of detecting interferents can be omitted if it is determined that the mitigation methodologies can be universally applied regardless of the presence of interferents or if the presence/effects of interferents are not relevant to the measurement. For example, sample cleaning can be a standard part of the measurement procedure regardless of whether an interferent has been detected. This can be advantageous in situations where a consistent measurement protocol is necessary or more advanced mitigation strategies are not warranted.

An interferent mitigation method can also involve determining the identities of one or more interferents present on or within the sample. Some example analysis methods for identifying the interferents are principal components analysis, neural networks, cluster analysis, K-Nearest Neighbors (KNN), and Discriminant analysis. The methods can be directly applied to the spectral measurement or to the multivariate calibration model residuals.

The additional information imparted by knowledge of the identities of one or more of the interferents present can be used to provide more specific instructions to the user. For example, if motor oil is determined to be on the surface of the sample, the present invention allows the user to be directed to use a motor oil-specific cleaner. Furthermore, knowledge of the identity of one or more interferents allows automatic or user-initiated modification of the multivariate calibration model or selection of a new multivariate calibration model in order to reduce the measurement error caused by the interferents.

If the identity or category of an interferent is known and a suitable spectral signature of the interferent is available, a multivariate calibration can be generated, for example by modification of a model built without regard to the specific interferent, such that the effects of the interferent are mathematically included in the model and are therefore substantially orthogonal to the analyte of interest. The spectral signature of the interferent can be derived directly from the sample measurement that the interferent is corrupting or from a reference library of interferent spectra or spectra representing interferent classes. The spectral signature of the interferent can be the spectroscopic signal of the interferent over the wavelength region of interest normalized to unit concentration and pathlength.

A multivariate model can be modified by orthogonal signal correction. Spectral data collected from complicated samples can contain variation from many sources. Orthogonal signal correction (OSC) is a pre-processing method that can be applied to help mitigate sources of variation orthogonal to the analyte of interest in order to make resulting models simpler and easier to interpret. In particular, OSC filters remove strong sources of variation in the spectra that are not correlated with the concentration of the analyte. An OSC filter is determined from a calibration set and applied to future spectral measurements prior to the application of the multivariate analyte model. Wold et al. published the original work on OSC which has been expanded upon by many other researchers. See, e.g., Wold S, Antti H, Lindgren F, Ohman J., "Orthogonal signal correction of near-infrared spectra," Chemometrics Intell. Lab. Syst., 1998; 44: 175-185, incorporated herein by reference.

Figure 13:
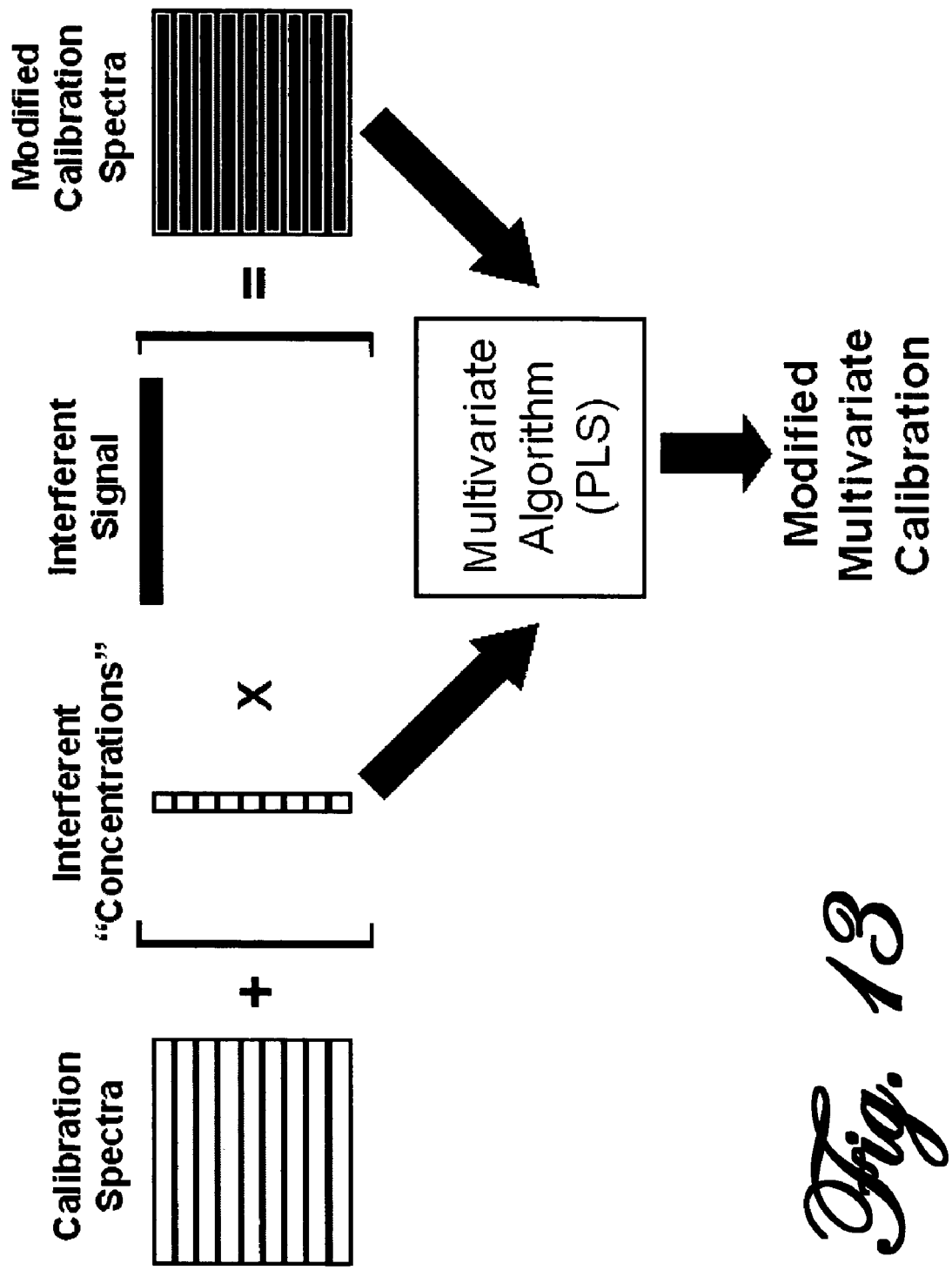
FIG. 13 is a diagram of an embodiment of the multivariate calibration model modification process.

A multivariate model can also be modified according to a "model modification procedure" as depicted in the schematic illustration of FIG. 13, which shows that the interferent's spectral signature mathematically added to previously-obtained calibration measurements prior to the use of the partial least squares algorithm. The vector of interferent concentrations can be based upon prior knowledge or generated randomly. The output of the partial least squares algorithm can then be applied to the previously acquired measurement or to subsequent measurements of the same sample. Such new measurements can follow other mitigation steps such as an interferent cleaning procedure.

A similar mathematical process can be used in situations where multiple interferents have been detected and identified. The concentrations of each interferent generally should be different than, and preferably uncorrelated with, the concentrations of other interferents added to the calibration data. Furthermore, not all detected interferents need to be identified and included for this approach to be beneficial. For example, if two interferents were detected, but only one could be reliably identified, the known interferent can still be treated using a modified multivariate calibration model.

Rather than mathematically including the spectral effects of an interferent, in some embodiments it is possible to re-acquire, or acquire new, calibration measurements. These measurements can be used to generate a new multivariate calibration model, or update an existing multivariate calibration model. Furthermore, it is recognized that multiple interferents can be present in a measurement. This process can be performed to mitigate one or all of the present interferents by incorporating as many interferents in the new measurements as are needed or desired.

Another aspect of altering the calibration is to include or exclude wavelengths of light from the calibration data based upon knowledge of the interferent from the calibration. The multivariate calibration model can then be regenerated and applied to the measured spectrum or subsequently measured spectra. In this manner, spectral regions dominated by the interferent can be excluded or additional wavelengths can be added to increase the amount of information available to resolve the interferent from the analyte.

Another interferent mitigation action involves the use of a library of multivariate calibration models that are designed to mitigate specific interferents or common combinations of interferents. These calibration models can be pre-determined such that detection and identification of a given interferent or combination of interferents allows selection of the appropriate multivariate calibration model for application to the same or subsequent measurements of a sample. This method allows the calibration data to be acquired with the interferents explicitly included in the measured calibration samples thereby directly including the spectral effects of the interferent(s) in the calibration.

In some embodiments, a library of pre-determined multivariate calibrations can be generated by combining interferent-free calibration data with various interferent spectral signatures in a manner similar to the mathematical combination approach in FIG. 13. Similar to the mathematical combination approach discussed above, the calibrations within the library can also include or exclude different wavelength regions in order to mitigate interferents. A "library" multivariate calibration model can be designed to mitigate more than 1 interferent and this method can be combined with one or more of the other mitigation steps.

Depending on the measurement, the number of potential interferents can be large. It can be advantageous to categorize interferents into a smaller number of representative classes in order to simplify the interferent mitigation strategy. The categorization can be based on spectroscopic signal or on chemical structure. For example, motor oil and grease are chemically and spectrally similar and can be placed in the same category. Other example categories include, but are not limited to, alcohols, medications, and skin lotions. Potential methods for assessing spectral similarity include, but are not limited to, classification methods such as K nearest neighbors, PCA, Discriminant analysis, and neural networks. The above described mitigation steps can be used to treat interferent categories rather than individual interferents. In some embodiments, interferents in the same category can be mitigated via the same methods and procedures while other classes can be mitigated with other methods and procedures.

Figure 14:
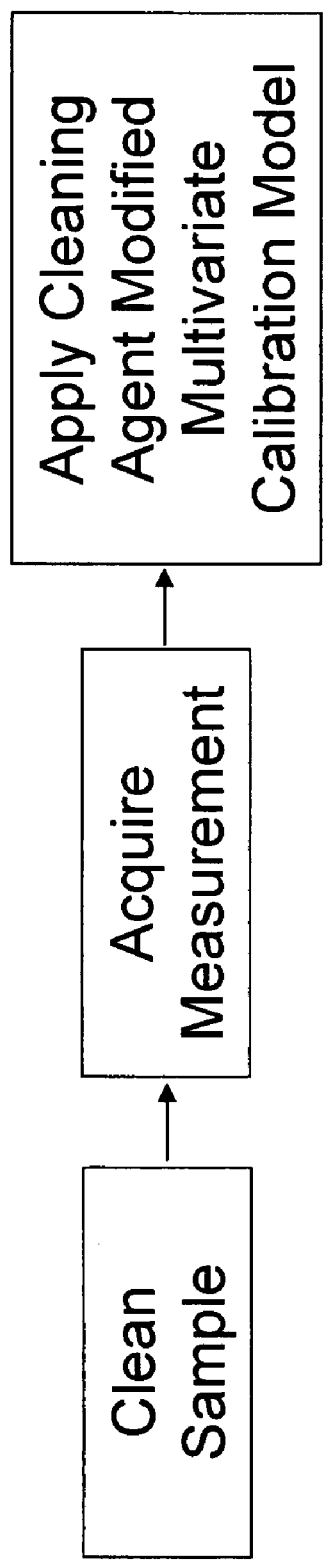
FIG. 14 is a schematic representation of an embodiment of an interferent mitigation method that is comprised of a sample cleaning step prior to the measurement and application of a cleaning agent modified multivariate calibration model.

FIGS. 14 through 19 show flow diagrams of some embodiments of interferent mitigation methods. FIG. 14 shows a simple method that includes cleaning the sample prior to measurement regardless of the potential presence of interferents, followed by measurement and application of a multivariate calibration model. In this example, the multivariate calibration model can include or exclude the spectral effects of the cleaning agent.

Figure 15:
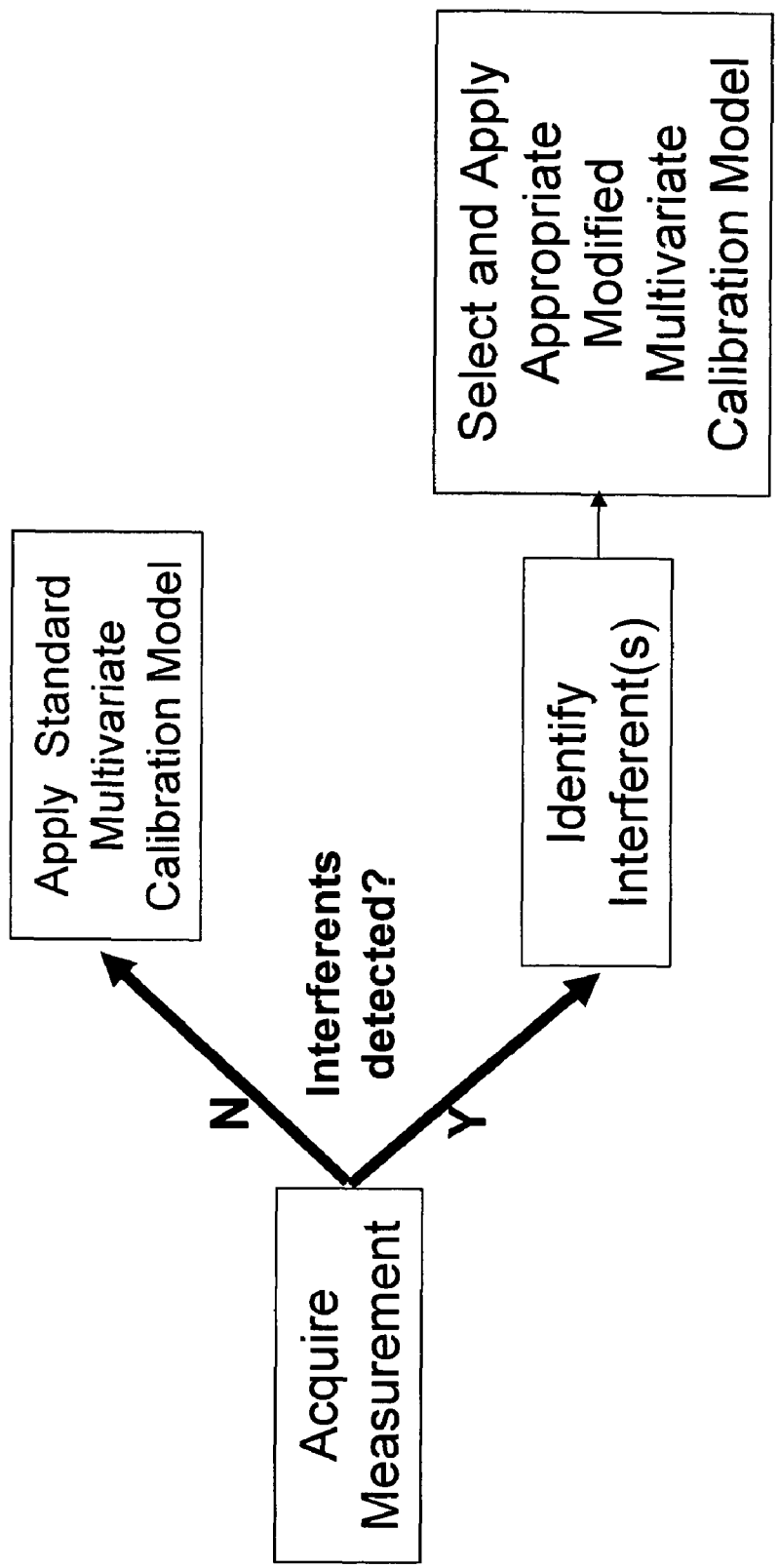
FIG. 15 is a schematic representation of an embodiment of an interferent mitigation method that is comprised of an interferent detection step and, upon interferent detection, interferent identification and multivariate calibration model selection steps.

FIG. 15 shows an example that includes interferent detection, identification, and calibration model modification steps. If no interferents are detected in the measurement, a multivariate calibration model is applied that includes no interferents or cleaning agent effects. If one or more interferents are detected, the measurement is analyzed to determine the identities of the interferents. While the flow diagrams show distinct detection and identification steps, some analysis techniques can simultaneously perform both actions. The spectral effects of the identified interferents can then be used to generate a suitable modified multivariate calibration model. The interferent identities can also be used to select a suitable multivariate calibration model from a library of such models.

Figure 16:
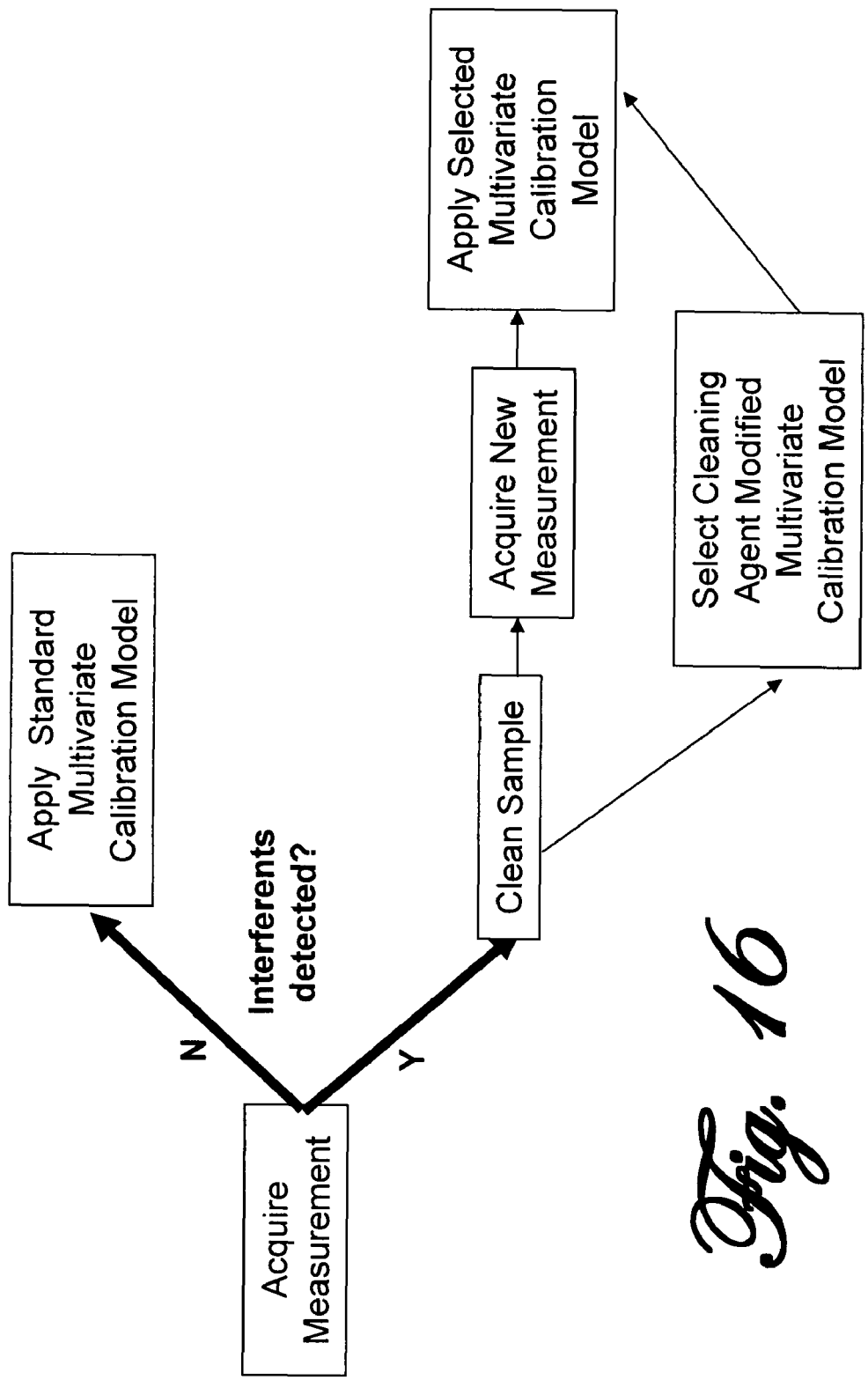
FIG. 16 is a schematic representation of an embodiment of an interferent mitigation method that is comprised of an interferent detection step and, upon interferent detection, a sample cleaning step followed by the acquisition of a new measurement and application of a cleaning agent modified multivariate calibration model.

FIG. 16 shows an embodiment of an interferent mitigation method involving a cleaning step that is performed only when interferents are detected. In this example, a new measurement is acquired following the cleaning procedure and a multivariate calibration model modified to include the spectral effects of the cleaning agent (or agents) is applied to the new measurement. Alternatively, the calibration models modified to accommodate a cleaning agent can be selected from a library of multivariate calibration models. Furthermore, this example can be extended to include multiple cleaning agents if desired.

Figure 17:
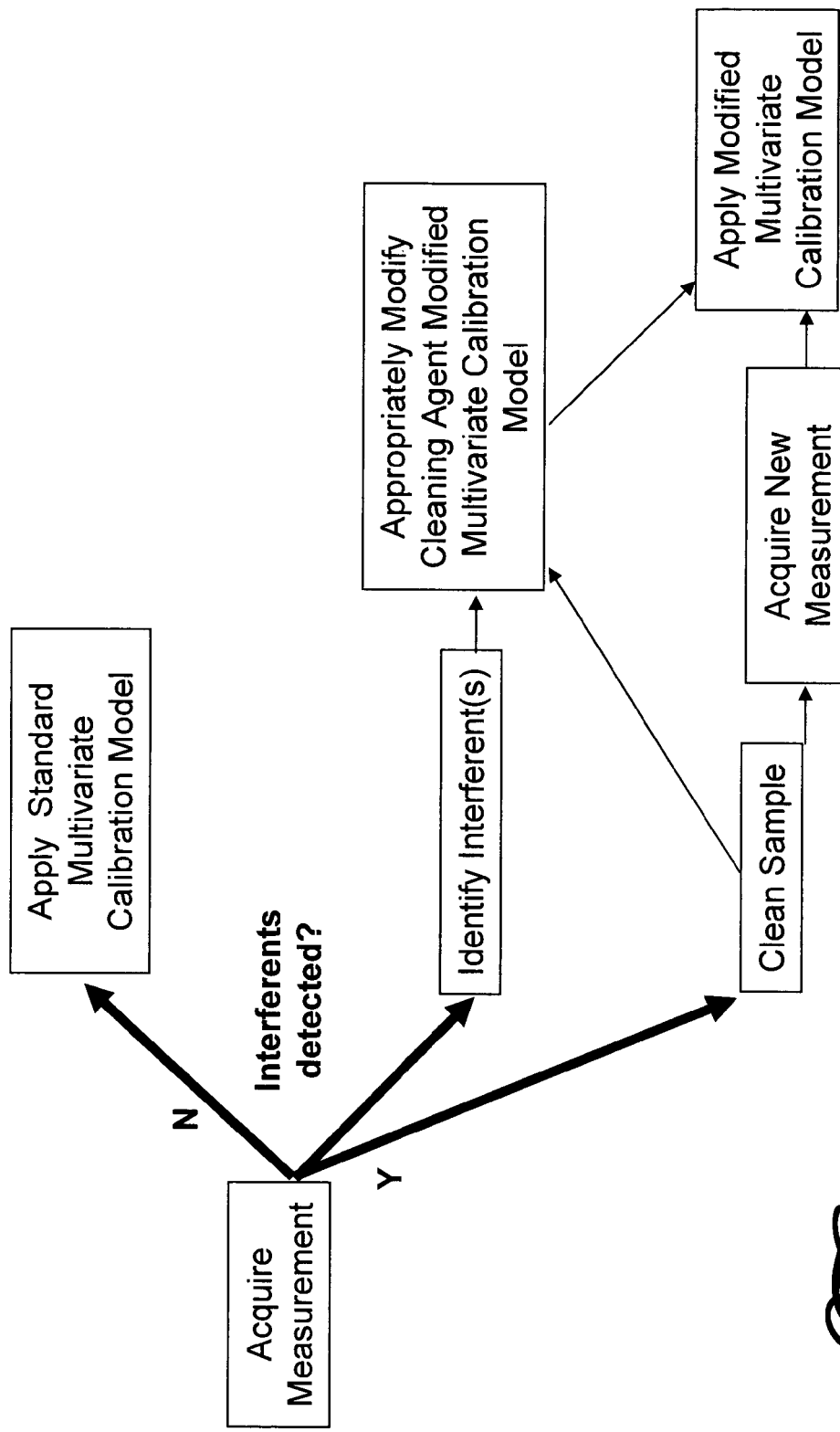
FIG. 17 is a schematic representation of an embodiment of an interferent mitigation method that is comprised of an interferent detection step and, upon interferent detection, parallel sample cleaning and interferent identification steps followed by the acquisition of a new measurement and application of an interferent and cleaning agent modified multivariate calibration model.

FIG. 17 shows an embodiment of an interferent mitigation method that combines the steps shown in FIGS. 15 and 16. In this embodiment, an interferent detection step is performed on a measurement. If an interferent is detected, both a sample cleaning procedure and an interferent identification step are performed in parallel. The multivariate calibration model is modified to include the spectral effects of the identified interferents and any cleaning agents used in the cleaning procedure. The multivariate calibration model can be selected from a predetermined library of multivariate calibration models. A new measurement is acquired from the cleaned sample and the modified multivariate calibration model is applied. FIG. 17 can be readily modified such that the sample cleaning step is determined based upon the identities of the detected interferents.

Figure 18:
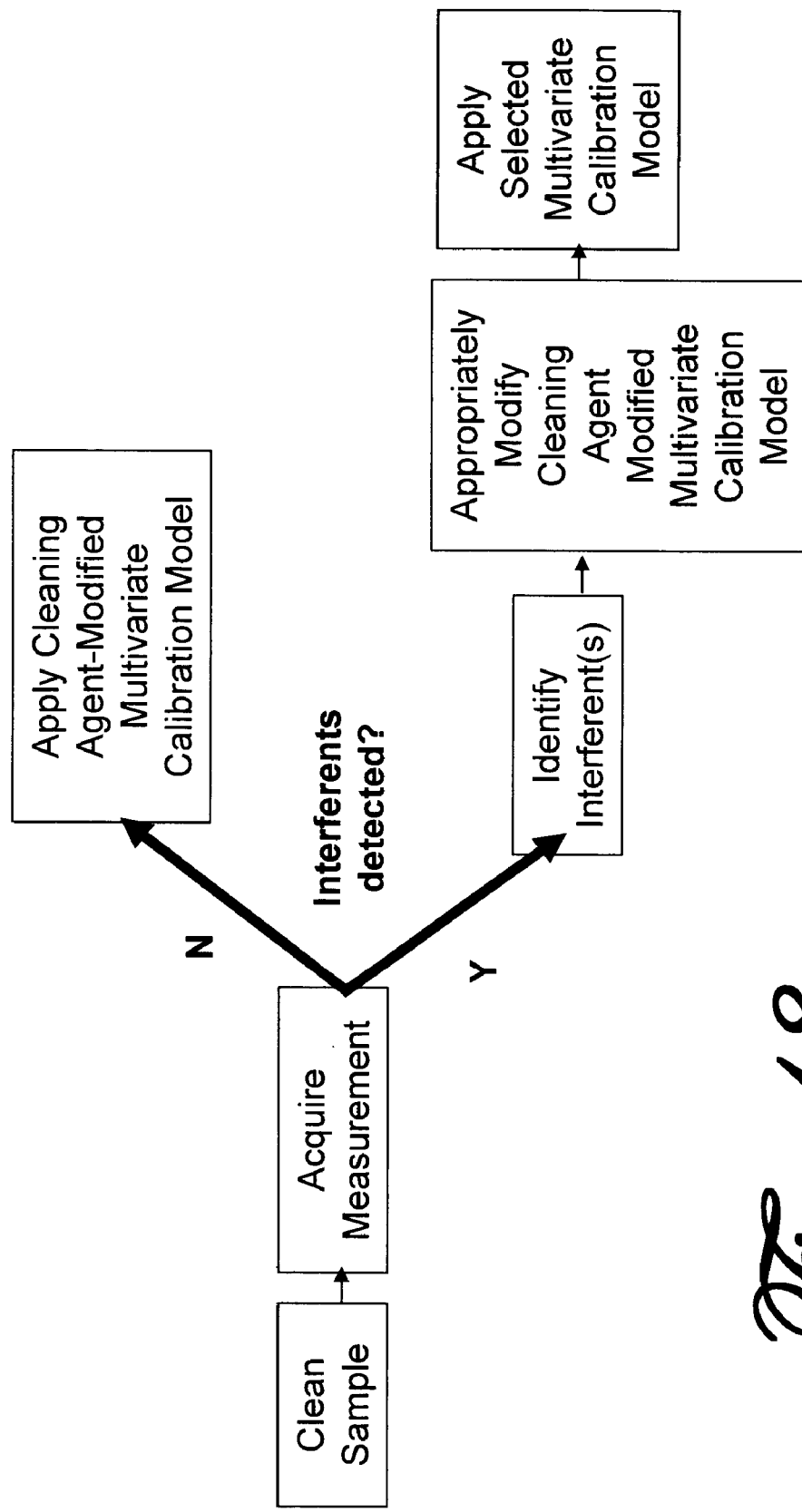
FIG. 18 is a schematic representation of an embodiment of an interferent mitigation method that is comprised of a mandatory sample cleaning step prior to the measurement followed by an interferent detection step and, upon interferent detection, an interferent identification steps followed by the application of an interferent and cleaning agent modified multivariate calibration model.

FIG. 18 shows an embodiment of an interferent mitigation method similar to the embodiment in FIG. 17, except that a sample cleaning procedure is performed regardless of whether interferents have been detected. The interferent detection step is still performed in order to determine if interferents remain a concern. If interferents are detected in the cleaned sample, the interferents are identified and the multivariate calibration model is suitably modified. FIG. 18 can be modified to show a second (or recursive) cleaning step in the event that interferents are detected.

Figure 19:
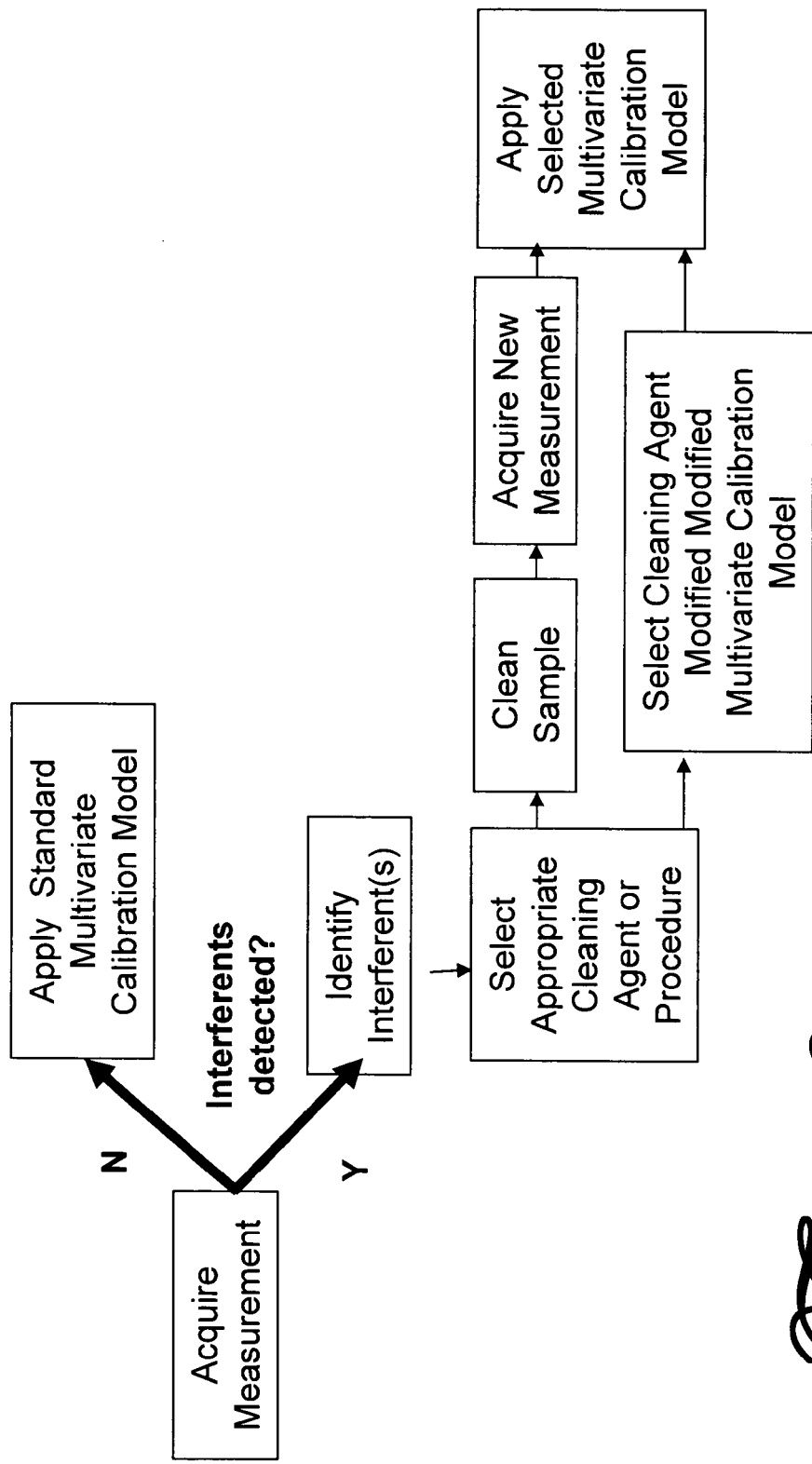
FIG. 19 is a schematic representation of an embodiment of an interferent mitigation method that is comprised of an interferent detection step and, upon interferent detection, an interferent identification step that specifies a sample cleaning step and the acquisition of a new measurement where an interferent and cleaning agent modified multivariate calibration model is applied.

FIG. 19 shows an embodiment of an interferent mitigation method where the identities of detected interferents are used to specify an appropriate cleaning procedure and/or cleaning agents. A new measurement is acquired from the cleaned sample and an appropriate cleaning agent modified multivariate calibration is applied. Similar to the embodiment of FIG. 18, FIG. 19 can be modified to show a second (or recursive) cleaning step in the event that interferents are detected in the cleaned sample.

Figure 20:
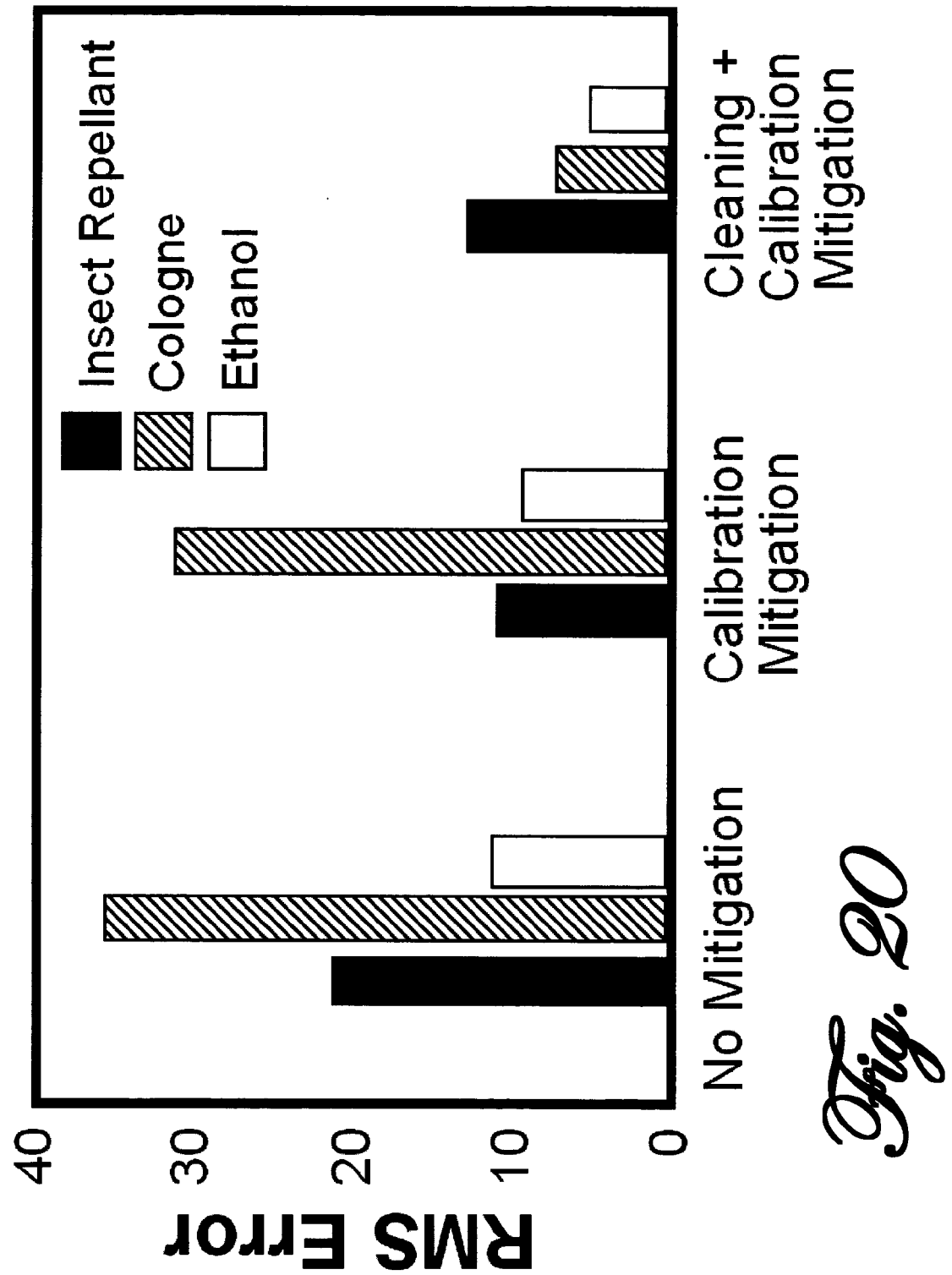
FIG. 20 shows clinical results that demonstrate the effectiveness of two interferent mitigation methods in noninvasive alcohol measurements.

FIG. 20 shows clinical results of noninvasive alcohol measurements using the interferent mitigation methods shown in FIGS. 15 and 16 and three different interferents. Each bar in FIG. 20 represents the root-mean-squared (RMS) alcohol error obtained from 30 measurements. The first set of bars (denoted "No Mitigation") represents the RMS error caused by each interferent when no interferent mitigation method was applied. In other words, the standard multivariate calibration model is blindly applied to the interferent-containing measurements. The second group of bars (denoted "Calibration Mitigation") is representative of the mitigation flow diagram in FIG. 15 and shows the RMS error for each interferent after the multivariate calibration was modified for that interferent using to the process shown in FIG. 13. All three bars in the second group are lower than the corresponding errors when no mitigation efforts were applied. The final group of bars (denoted "Cleaning+Calibration Mitigation") represents the mitigation method shown in FIG. 16 where the interferents were detected, a cleaning procedure was initiated, and a multivariate calibration model incorporating the spectral effects of the cleaning agent was applied. A disposable isopropyl alcohol wipe was used in the cleaning procedure. Again, the three bars in the third group are lower than the corresponding errors when no mitigation efforts were applied.

New characteristics and advantages of the invention covered by this document have been set forth in the foregoing description. It will be understood, however, that this disclosure is, in many respects, only illustrative. Changes can be made in details, particularly in matters of shape, size, and arrangement of parts or steps, without exceeding the scope of the invention. The scope of the invention is, of course, defined in the language in which the appended claims are expressed.

What is claimed is:

1. A method for determining an analyte property in a biological subject, comprising:
   a) Determining a spectrum, comprising information related to the response of a portion of the subject to incident radiation;
   b) Determining from the spectrum without a contemporaneous reference value whether an interferent affected the spectrum (an "interferent condition"), and, if so, performing an interferent mitigation action;
   c) Determining the analyte property in the biological subject from the spectrum after steps a) and b).

2. A method as in claim 1, wherein determining from the spectrum whether an interferent affected the spectrum comprises determining an outlier metric of the spectrum, and determining whether the outlier metric has a value corresponding to an interferent condition.

3. A method as in claim 1, wherein determining from the spectrum whether an interferent affected the spectrum comprises determining the analyte property in the biological subject, and determining whether the analyte property has a value corresponding to interferent conditions.

4. A method as in claim 1, wherein determining from the spectrum whether an interferent affected the spectrum comprises applying to the spectrum a model relating a spectrum to presence of an interferent, and from the result determining whether the spectrum indicates an interferent condition.

5. A method as in claim 1, wherein the spectrum comprises response of a portion of the subject at first and second paths through the portion of the subject, and wherein determining from the spectrum whether an interferent affected the spectrum comprises determining an interferent condition from comparison of the spectrum at the first path with the spectrum at the second path.

6. A method as in claim 1, wherein determining the analyte property in the biological subject comprises determining the analyte property from a model relating a spectrum to the analyte property, and wherein the interferent mitigation action comprises selecting a model for determination of the analyte property that is resistant to interferent effects.

7. A method as in claim 1, wherein determining the analyte property in the biological subject comprises determining the analyte property from a model relating a spectrum to the property and wherein the interferent mitigation action comprises changing a model for determination of the analyte property in a way that decreases the effect of the interferent on the determination of the analyte property.

8. A method as in claim 1, wherein the analyte property comprises the concentration or presence of alcohol, the biological subject comprises human tissue, and the spectrum comprises the response of the tissue to near-infrared light.

9. A method as in claim 8, wherein determining the analyte property in the biological subject after the interferent mitigation action comprises applying a multivariate model relating alcohol concentration or presence to a spectrum of response to near-infrared light.

10. A method of determining an analyte property in a biological subject when there is no interferent present, comprising:
    a) Determining a spectrum of a portion of the subject, where the spectrum comprises information regarding the response at a plurality of wavelengths of the portion of the subject to incident radiation;
    b) Determining from the spectrum without a contemporaneous reference value whether an interferent is present, where an interferent is any foreign substance that unacceptably compromises the quality of the determination of the characteristic;
    c) If there is no interferent present, then determining the analyte property from the spectrum.

11. A method as in claim 10, wherein determining from the spectrum whether an interferent is present comprises at least one of:
    a) Determining whether the spectral F-ratio of the spectrum relative to a plurality of calibration spectra has a value that indicates an interferent is present;
    b) Determining whether a multidimensional distance between the spectrum and a calibration spectrum has a value that indicates an interferent is present;
    c) Determining whether the Mahalanobis distance from the spectrum to a plurality of calibration spectra has a value that indicates an interferent is present.

12. A method as in claim 10, wherein determining from the spectrum whether an interferent is present comprises applying to the spectrum at least one of the following methods of analysis: a neural network, residuals of principal component analysis, and k-nearest neighbors.

13. A method as in claim 10, further comprising classifying the interferent, if one is determined to be present.

14. A method as in claim 12, further comprising communicating the classification of the interferent to a user.

15. A method of determining an analyte property in a biological subject, comprising:
    a) Determining a spectrum of a portion of the subject, where the spectrum comprises information regarding the response at a plurality of wavelengths of the portion of the subject to incident radiation;
    b) Determining from the spectrum whether an interferent is present, where an interferent is any foreign substance that unacceptably compromises the quality of the determination of the property;
    c) If an interferent is present, then classifying the interferent from the spectrum;
    d) Selecting a method of determining the analyte property from the determination of the presence of an interferent and, if an interferent is present, also from the classification of the interferent;
    e) Determining the analyte property from the spectrum and from the selected method.

16. A method as in claim 15, wherein classifying the interferent comprises at least one of: k-nearest neighbors, principal components analysis, and a neural network.

17. A method as in claim 15, wherein selecting a method comprises using a multivariate model to determine the analyte property, wherein, if an interferent is detected, a multivariate model resistant to the effect of the classified interferent is used.

18. A method as in claim 17, wherein the multivariate model resistant to the effect of the classified interferent comprises a model generated from data including the presence of the classified interferent.

19. A method as in claim 17, wherein the multivariate model resistant to the effect of the classified interferent comprises a multivariate model modified using orthogonal signal correction.

20. A method as in claim 17, wherein the multivariate model resistant to the effect of the classified interferent comprises a multivariate model modified using a model modification procedure.

21. A method as in claim 15, wherein selecting a method comprises using a multivariate model to determine the analyte property, wherein, if an interferent is detected, a base multivariate model is modified before use to be resistant to the effect of the classified interferent.

22. A method as in claim 21, wherein the base multivariate model is modified using orthogonal signal correction.

23. A method as in claim 21, wherein the base multivariate model is modified using a model modification procedure.

24. A method as in claim 15, wherein selecting a method of determining the analyte property from the determination of the presence of an interferent comprises selecting a method without a contemporaneous reference value of the analyte property.

* * * * *